US006780477B2

(12) United States Patent
Kirsch et al.

(10) Patent No.: US 6,780,477 B2
(45) Date of Patent: Aug. 24, 2004

(54) LIQUID CRYSTALLINE COMPOUNDS

(75) Inventors: Peer Kirsch, Seeheim-Jugenheim (DE); Detlef Pauluth, Ober-Ramstadt (DE); Joachim Krause, Dieburg (DE); Michael Heckmeier, Hemsbach (DE); Georg Lüssem, Ober-Ramstadt (DE); Dagmar Klement, Gross-Zimmern (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/450,267

(22) PCT Filed: Oct. 1, 2001

(86) PCT No.: PCT/EP01/11322

§ 371 (c)(1),
(2), (4) Date: Jun. 12, 2003

(87) PCT Pub. No.: WO02/48081

PCT Pub. Date: Jun. 20, 2002

(65) Prior Publication Data

US 2004/0046150 A1 Mar. 11, 2004

(30) Foreign Application Priority Data

Dec. 12, 2000 (DE) .......................................... 100 61 790

(51) Int. Cl.[7] ......................... C09K 19/30; C09K 19/34; C09K 19/32; C07C 25/13; C07C 25/18
(52) U.S. Cl. .............. 428/1.1; 252/299.61; 252/299.62; 252/299.63; 570/129; 570/130; 570/131
(58) Field of Search .................................. 570/127, 130, 570/129, 131; 252/299.61, 299.63; 428/1.1

(56) References Cited

U.S. PATENT DOCUMENTS 5,792,386 A 8/1998 Matsui et al.
6,630,210 B2 * 10/2003 Kirsch et al. ................ 428/1.1

FOREIGN PATENT DOCUMENTS

DE 19814550 10/1999
EP 0786445 7/1997

OTHER PUBLICATIONS

CAPLUS 2001: 872309.*

* cited by examiner

Primary Examiner—Shean C. Wu
(74) Attorney, Agent, or Firm—Millen, White, Zelano, Branigan, P.C.

(57) ABSTRACT

The invention relates to liquid-crystalline compounds of the formula I

I

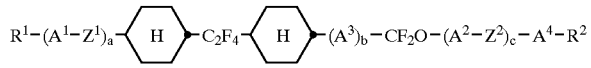

in which $R^1$, $R^2$, $A^1$, $A^2$, $A^3$, $A^4$, $Z^1$, $Z^2$, a, b and c are as defined in claim 1, and to liquid-crystalline media comprising at least compound of the formula I and to electro-optical displays containing a liquid-crystalline medium of this type.

36 Claims, No Drawings

LIQUID CRYSTALLINE COMPOUNDS

The present invention relates to liquid-crystalline compounds and to a liquid-crystalline medium, to the use thereof for electro-optical purposes, and to displays containing this medium.

Liquid-crystals are used principally as dielectrics in display devices, since the optical properties of such substances can be modified by an applied voltage. Electro-optical devices based on liquid crystals are extremely well known to the person skilled in the art and can be based on various effects. Examples of such devices are cells having dynamic scattering, DAP (deformation of aligned phases) cells, guest/host cells, TN cells having a twisted nematic structure, STN (supertwisted nematic) cells, SBE (super-birefringence effect) cells and OMI (optical mode interference) cells. The commonest display devices are based on the Schadt-Helfrich effect and have a twisted nematic structure.

The liquid-crystal materials must have good chemical and thermal stability and good stability to electric fields and electromagnetic radiation. Furthermore, the liquid-crystal materials should have low viscosity and produce short addressing times, low threshold voltages and high contrast in the cells.

They should furthermore have a suitable mesophase, for example a nematic or cholesteric mesophase for the above-mentioned cells, at the usual operating temperatures, i.e. in the broadest possible range above and below room temperature. Since liquid crystals are generally used as mixtures of a plurality of components, it is important that the components are readily miscible with one another. Further properties, such as the electrical conductivity, the dielectric anisotropy and the optical anisotropy, have to satisfy various requirements depending on the cell type and area of application. For example, materials for cells having a twisted nematic structure should have positive dielectric anisotropy and low electrical conductivity.

For example, for matrix liquid-crystal displays with integrated non-linear elements for switching individual pixels (MLC displays), media having large positive dielectric anisotropy, broad nematic phases, relatively low birefringence, very high specific resistance, good UV and temperature stability and low vapour pressure are desired.

Matrix liquid-crystal displays of this type are known. Non-linear elements which can be used for individual switching of the individual pixels are, for example, active elements (i.e. transistors). The term "active matrix" is then used, where a distinction can be made between two types:

1. MOS (metal oxide semiconductor) or other diodes on a silicon wafer as substrate.

2. Thin-film transistors (TFTs) on a glass plate as substrate.

The use of single-crystal silicon as substrate material restricts the display size, since even modular assembly of various part-displays results in problems at the joins.

In the case of the more promising type 2, which is preferred, the electro-optical effect used is usually the TN effect. A distinction is made between two technologies: TFTs comprising compound semiconductors, such as, for example, CdSe, or TFTs based on polycrystalline or amorphous silicon. Intensive work is being carried out worldwide on the latter technology.

The TFT matrix is applied to the inside of one glass plate of the display, while the other glass plate carries the transparent counterelectrode on its inside. Compared with the size of the pixel electrode, the TFT is very small and has virtually no adverse effect on the image. This technology can also be extended to fully colour-capable displays, in which a mosaic of red, green and blue filters is arranged in such a way that a filter element is opposite each switchable pixel.

The TFT displays usually operate as TN cells with crossed polarisers in transmission and are illuminated from the back.

The term MLC displays here covers any matrix display with integrated non-linear elements, i.e., besides the active matrix, also displays with passive elements, such as varistors or diodes (MIM=metal-insulator-metal).

MLC displays of this type are particularly suitable for TV applications (for example pocket TVs) or for high-information displays for computer applications (laptops) and in automobile or aircraft construction. Besides problems regarding the angle dependence of the contrast and the response times, difficulties also arise in MLC displays due to insufficiently high specific resistance of the liquid-crystal mixtures [TOGASHI, S., SEKIGUCHI, K., TANABE, H., YAMAMOTO, E., SORIMACHI, K., TAJIMA, E., WATANABE, H., SHIMIZU, H., Proc. Eurodisplay 84, September 1984: A 210–288 Matrix LCD Controlled by Double Stage Diode Rings, p. 141 ff, Paris; STROMER, M., Proc. Eurodisplay 84, September 1984: Design of Thin Film Transistors for Matrix Addressing of Television Liquid Crystal Displays, p. 145 ff, Paris]. With decreasing resistance, the contrast of an MLC display deteriorates, and the problem of after-image elimination may occur. Since the specific resistance of the liquid-crystal mixture generally drops over the life of an MLC display owing to interaction with the interior surfaces of the display, a high (initial) resistance is very important in order to obtain acceptable service lives. In particular in the case of low-volt mixtures, it was hitherto impossible to achieve very high specific resistance values. It is furthermore important that the specific resistance exhibits the smallest possible increase with increasing temperature and after heating and/or UV exposure. The low-temperature properties of the mixtures from the prior art are also particularly disadvantageous. It is demanded that no crystallisation and/or smectic phases occur, even at low temperatures, and the temperature dependence of the viscosity is as low as possible. The MLC displays from the prior art thus do not meet today's requirements.

Besides liquid-crystal displays which use backlighting, i.e. are operated transmissively and possibly transflectively, reflective liquid-crystal displays are also particularly interesting. These reflective liquid-crystal displays use the ambient light for display of information. They consequently consume significantly less energy than backlit liquid-crystal displays of corresponding size and resolution. Since the TN effect is characterised by very good contrast, reflective displays of this type are still readily legible even in bright ambient conditions. This is already known of simply reflective TN displays, as used, for example, in wristwatches and pocket calculators. However, the principle can also be applied to high-quality active matrix-addressed displays of higher resolution, such as, for example, TFT displays. Here, as already in the transmissive TFT-TN displays that are generally usual, the use of liquid crystals of low birefringence ($\Delta n$) is necessary in order to achieve low optical retardation ($d \cdot \Delta n$). This low optical retardation leads to a low viewing-angle dependence of the contrast that is usually acceptable (cf. DE 30 22 818). In reflective displays, the use of liquid crystals of low birefringence is even more important than in the case of transmissive displays since in reflective displays the effective layer thickness through which the light passes is approximately twice as great as in transmissive displays having the same layer thickness.

There thus continues to be a great demand for MLC displays having very high specific resistance at the same time as a large working-temperature range, short response times even at low temperatures and low threshold voltage which do not have these disadvantages, or only do so to a reduced extent.

In TN (Schadt-Helfrich) cells, media are desired which facilitate the following advantages in the cells:

low optical birefringence (Δn) for reflective applications extended nematic phase range (in particular down to low temperatures)

the ability to switch at extremely low temperatures (outdoor use, automobile, avionics)

increased resistance to UV radiation (longer service life)

low rotational viscosity for short switching times.

In the case of supertwisted (STN) cells, media are desired which enable greater multiplexability and/or lower threshold voltages and/or broader nematic phase ranges (in particular at low temperatures). To this end, a further widening of the available parameter latitude (clearing point, smectic-nematic transition or melting point, viscosity, dielectric parameters, elastic parameters) is urgently desired.

The invention has the object of providing media, in particular for MLC, TN or STN displays of this type, which do not have the above-mentioned disadvantages or only do so to a reduced extent, and preferably simultaneously have very high specific resistances and low threshold voltages. This object requires liquid-crystalline compounds which have a high clearing point and low rotational viscosity.

The media available from the prior art do not allow these advantages to be achieved while simultaneously retaining the other parameters.

It has now been found that this object can be achieved if the liquid-crystalline compounds according to the invention are used.

The invention thus relates to liquid-crystalline compounds of the formula I

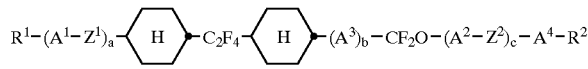

I in which $R^1$ and $R^2$ are each, independently of one another, an alkyl radical having from 1 to 15 carbon atoms which is unsubstituted, monosubstituted by CN or $CF_3$ or at least monosubstituted by halogen, where, in addition, one or more $CH_2$ groups in these radicals may be replaced by —O—, —S—, —CH═CH—, —C≡C—, —OC—O— or —O—CO— in such a way that O atoms are not linked directly to one another, and $R^2$ is alternatively CN, $SF_5$, F, Cl, NCS or SCN, $A^1$, $A^2$, $A^3$ and $A^4$ are a) a 1,4-cyclohexenylene or 1,4-cyclohexylene radical, in which one or two non-adjacent $CH_2$ groups may be replaced by —O— or —S—, b) a 1,4-phenylene radical, in which one or two CH groups may be replaced by N, c) a radical from the group consisting of piperidine-1,4-diyl 1,4-bicyclo[2.2.2]octylene, naphthalene-2,6-diyl, decahydronaphthalene-2,6-diyl and 1,2,3,4-tetrahydronaphthalene-2,6-diyl, where the radicals a), b) and c) may be monosubstituted or polysubstituted by halogen atoms, $Z^1$ and $Z^2$ are each, independently of one another, —CO—O—, —O—CO—, —$CF_2$O—, —O$CF_2$—, —$CH_2$O—, —O$CH_2$—, —$CH_2CH_2$—, —$(CH_2)_4$—, —$C_2F_4$—, —$CH_2CF_2$—, —$CF_2CH_2$—, —CF═CF—, —CH═CH—, —C≡C— or a single bond, a is 0, 1 or 2, b is 0, 1 or 2, and c is 0, 1 or 2, where a+b+c is ≦2.

The invention furthermore relates to the use of the compounds of the formula I in liquid-crystalline media.

The compounds of the formula I have a broad range of applications. Depending on the choice of substituents, these compounds can serve as base materials of which liquid-crystalline media are predominantly composed; however, it is also possible to add compounds of the formula I to liquid-crystalline base materials from other classes of compound in order, for example, to modify the dielectric and/or optical anisotropy of a dielectric of this type and/or in order to optimise its threshold voltage and/or its viscosity.

In the pure state, the compounds of the formula I are colourless and form liquid-crystalline mesophases in a temperature range which is favourably located for electro-optical use. In particular, the compounds according to the invention are distinguished by their high clearing point and their low values for the rotational viscosity. They are stable chemically, thermally and to light.

The invention relates in particular to the compounds of the formula I in which $R^1$ is alkyl having from 1 to 10 carbon atoms or an alkenyl radical having from 2 to 10 carbon atoms.

Particular preference is given to compounds of the formula I in which c=0. $Z^1$ and $Z^2$ are preferably a single bond, furthermore —$CF_2$O—, —O$CF_2$—, —$C_2F_4$—, —$CH_2$O—, —O$CH_2$— or —COO—. a is preferably 0.

If $R^1$ and/or $R^2$ is an alkyl radical and/or an alkoxy radical, this may be straight-chain or branched. It is preferably straight-chain, has 2, 3, 4, 5, 6 or 7 carbon atoms and accordingly is preferably ethyl, propyl, butyl, pentyl, hexyl, heptyl, ethoxy, propoxy, butoxy, pentoxy, hexyloxy or heptyloxy, furthermore methyl, octyl, nonyl, decyl, undecyl, dodecyl, tridecyl, tetradecyl, pentadecyl, methoxy, octyloxy, nonyloxy, decyloxy, undecyloxy, dodecyloxy, tridecyloxy or tetradecyloxy.

Oxaalkyl is preferably straight-chain 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-,4-, 5-, 6-, 7- or 8-oxanonyl, or 2-, 3-, 4-, 5-, 6-, 7-, 8- or 9-oxadecyl.

If $R^1$ and/or $R^2$ is an alkenyl radical, this may be straight-chain or branched. It is preferably straight-chain and has from 2 to 10 carbon atoms. Accordingly, it is in particular vinyl, prop-1- or -2-enyl, but-1-, -2- or -3-enyl, pent-1-, -2-, -3- or -4-enyl, hex-1-, -2-, -3-, 4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, or dec-1-, -2-, -3-, -4-, -5-, -6-, -7-, -8- or -9-enyl.

If $R^1$ and/or $R^2$ is an alkyl radical in which one $CH_2$ group has been replaced by —O— and one has been replaced by —CO—, these are preferably adjacent. These thus contain an acyloxy group —CO—O— or an oxycarbonyl group —O—CO. These are preferably straight-chain and have from 2 to 6 carbon atoms.

Accordingly, they are in particular acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl or 4-(methoxycarbonyl)butyl.

If $R^1$ and/or $R^2$ is an alkyl or alkenyl radical which is monosubstituted by CN or $CF_3$, this radical is preferably straight-chain. The substitution by CN or $CF_3$ is in any desired position.

If $R^1$ and/or $R^2$ is an alkyl or alkenyl radical which is at least monosubstituted by halogen, this radical is preferably straight-chain, and halogen is preferably F or Cl. In the case of polysubstitution, halogen is preferably F. The resultant radicals also include perfluorinated radicals. In the case of monosubstitution, the fluorine or chlorine substituent may be in any desired position, but is preferably in the ω-position.

Compounds of the formula I containing branched wing groups $R^1$ and/or $R^2$ may occasionally be of importance owing to better solubility in the conventional liquid-crystalline base materials, but in particular as chiral dopants if they are optically active. Smectic compounds of this type are suitable as components of ferroelectric materials.

Compounds of the formula I having $S_A$ phases are suitable for thermally addressed displays.

Branched groups of this type generally contain not more than one chain branch. Preferred branched radicals $R^1$ and/or $R^2$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexyloxy, 1-methylhexyloxy and 1-methylheptyloxy.

$R^2$ is preferably F, Cl, CN, $CF_3$, $SF_5$, $CF_2H$, $OCF_3$, $OCF_2H$, $OCFHCF_3$, $OCFHCFH_2$, $OCFHCF_2H$, $OCF_2CH_3$, $OCF_2CFH_2$, $OCF_2CF_2H$, $OCF_2CF_2CF_2H$, $OCF_2CF_2CFH_2$, $OCFHCF_2CF_3$, $OCFHCF_2CF_2H$, $OCFHCF_2CF_2H$, $OCFHCF_2CF_2H$, $OCH_2CF_2CF_3$, $OCF_2CF_2CF_3$, $OCF_2CFHCFH_2$, $OCF_2CH_2CF_2H$, $OCFHCF_2CFH_2$, $OCFHCFHCF_2H$, $OCFHCH_2CF_3$, $OCH_2CFHCF_3$, $OCH_2CF_2CF_2H$, $OCF_2CFHCH_3$, $OCF_2CH_2CFH_2$, $OCFHCF_2CH_3$, $OCFHCFHCFH_2$, $OCFHCH_2CF_3$, $OCH_2CF_2CFH_2$, $OCH_2CFHCF_2H$, $OCF_2CH_2CH_3$, $OCFHCFHCH_3$, $OCFHCH_2CFH_2$, $OCH_2CF_2CH_3$, $OCH_2CFHCFH_2$, $OCH_2CH_2CF_2H$, $OCHCH_2CH_3$, $OCH_2CFHCH_3$, $OCH_2CH_2CFH_2$, $OCClFCF_3$, $OCClFCClF_2$, $OCClFCFH_2$, $OCFHCCl_2F$, $OCClFCF_2H$, $OCClFCClF_2$, $OCF_2CClH_2$, $OCF_2CCl_2H$, $OCF_2CCl_2F$, $OCF_2CClFH$, $OCF_2CClF_2$, $OCF_2CF_2CClF_2$, $OCF_2CF_2CCl_2F$, $OCClFCF_2CF_3$, $OCClFCF_2CF_2H$, $OCClFCF_2CClF_2$, $OCClFCFHCF_3$, $OCClFCClFCF_3$, $OCCl_2CF_2CF_3$, $OCClHCF_2CF_3$, $OCClFCF_2CF_3$, $OCClFCClFCF_3$, $OCF_2CClFCFH_2$, $OCF_2CF_2CCl_2F$, $OCF_2CCl_2CF_2H$, $OCF_2CH_2CClF_2$, $OCClFCF_2CFH_2$, $OCFHCF_2CCl_2F$, $OCClFCFHCF_2H$, $OCClFCClFCF_2H$, $OCFHCFHCClF_2$, $OCClFCH_2CF_3$, $OCFHCCl_2CF_3$, $OCCl_2CFHCF_3$, $OCH_2CClFCF_3$, $OCCl_2CF_2CF_2H$, $OCH_2CF_2CClF_2$, $OCF_2CClFCH_3$, $OCF_2CFHCCl_2H$, $OCF_2CCl_2CFH_2$, $OCF_2CH_2CCl_2F$, $OCClFCF_2CH_3$, $OCFHCF_2CCl_2H$, $OCClFCClFCFH_2$, $OCFHCFHCCl_2F$, $OCClFCH_2CF_3$, $OCCl_2CF_2CFH_2$, $OCH_2CF_2CCl_2F$, $OCCl_2CFHCF_2H$, $OCClHCClFCF_2H$, $OCF_2CH_2CCl_2H$, $OCClFCFHCH_3$, $OCF_2CClFCClH_2$, $OCF_2CH_2CCl_2H$, $OCClFCFHCH_3$, $OCFHCCl_2CFH_2$, $OCH_2CCl_2CF_2H$, $OCClFCH_2CH_3$, $OCFHCH_2CCl_2H$, $OCClHCFHCClH_2$, $OCH_2CFHCCl_2H$, $OCCl_2CH_2CF_2H$, $OCH_2CCl_2CF_2H$, $CH=CF_2$, $CF=CF_2$, $OCH=CF_2$, $OCF=CF_2$, $CH=CHF$, $OCH=CHF$, $CF=CHF$ or $OCF=CHF$, in particular F, Cl, CN, $CF_3$, $SF_5$, $CF_2H$, $OCF_3$, $OCF_2H$, $OCFHCF_3$, $OCFHCFH_2$, $OCFHCF_2H$, $OCF_2CH_3$, $OCF_2CFH_2$, $OCF_2CF_2H$, $OCF_2CF_2CF_2H$, $OCF_2CF_2CFH_2$, $OCFHCF_2CF_3$, $OCFHCF_2CF_2H$, $OCF_2CF_2CF_3$, $OCF_2CHFCF_3$ or $OCClFCF_2CF_3$.

For reasons of simplicity, Cyc below denotes a 1,4-cyclohexylene radical, Che denotes a 1,4-cyclohexenylene radical, Dio denotes a 1,3-dioxane-2,5-diyl radical, Dit denotes a 1,3-dithiane-2,5-diyl radical, Phe denotes a 1,4-phenylene radical, Pyd denotes a pyridine-2,5-diyl radical, Pyr denotes a pyrimidine-2,5-diyl radical, Bi denotes a bicyclo[2.2.2]octylene radical, PheF denotes a 2- or 3-fluoro-1,4-phenylene radical, PheFF denotes a 2,3-difluoro- or 2,6-difluoro-1,4-phenylene radical, Nap denotes a substituted or unsubstituted naphthalene radical, and Dec denotes a decahydro-naphthalene radical.

The compounds of the formula I accordingly include the preferred tricyclic compounds of the sub-formulae Ia to Ig:

| | |
|---|---|
| $R^1$-Cyc-$C_2F_4$-Cyc-$CF_2$O-Phe-$R^2$ | Ia |
| $R^1$-Cyc-$C_2F_4$-Cyc-$CF_2$O-PheF-$R^2$ | Ib |
| $R^1$-Cyc-$C_2F_4$-Cyc-$CF_2$O-PheFF-$R^2$ | Ic |
| $R^1$-Cyc-$C_2F_4$-Cyc-$CF_2$O-Bi-$R^2$ | Id |
| $R^1$-Cyc-$C_2F_4$-Cyc-$CF_2$O-Nap-$R^2$ | Ie |
| $R^1$-Cyc-$C_2F_4$-Cyc-$CF_2$O-Dec-$R^2$ | If |
| $R^1$-Cyc-$C_2F_4$-Cyc-$CF_2$O-Bi-$R^2$ | Ig | and tetracyclic compounds of the sub-formulae Ih to Iw:

| | |
|---|---|
| $R^1$-Cyc-$C_2F_4$-Cyc-Cyc-$CF_2$O-Phe-$R^2$ | Ih |
| $R^1$-Cyc-$C_2F_4$-Cyc-Cyc-$CF_2$O-PheF-$R^2$ | Ii |
| $R^1$-Cyc-$C_2F_4$-Cyc-Cyc-$CF_2$O-PheFF-$R^2$ | Ij |
| $R^1$-Cyc-$C_2F_4$-Cyc-Cyc-$CF_2$O-Phe-$R^2$ | Ik |
| $R^1$-Cyc-$C_2F_4$-Cyc-Cyc-$CF_2$O-PheF-$R^2$ | Il |
| $R^1$-Cyc-$C_2F_4$-Cyc-Cyc-$CF_2$O-PheFF-$R^2$ | Im |
| $R^1$-Cyc-$C_2F_4$-Cyc-Cyc-$CF_2$O-Nap-$R^2$ | In |
| $R^1$-Cyc-$C_2F_4$-Cyc-Cyc-$CF_2$O-Dec-$R^2$ | Io |
| $R^1$-Cyc-$C_2F_4$-Cyc-Cyc-$CF_2$O-Bi-$R^2$ | Ip |
| $R^1$-Cyc-$C_2F_4$-Cyc-Phe-$CF_2$O-Phe-$R^2$ | Iq |
| $R^1$-Cyc-$C_2F_4$-Cyc-Phe-$CF_2$O-PheF-$R^2$ | Ir |
| $R^1$-Cyc-$C_2F_4$-Cyc-Phe-$CF_2$O-PheFF-$R^2$ | Is |
| $R^1$-Cyc-$C_2F_4$-Cyc-PheF-$CF_2$O-Phe-$R^2$ | It |
| $R^1$-Cyc-$C_2F_4$-Cyc-PheFF-$CF_2$O-Phe-$R^2$ | Iu |
| $R^1$-Cyc-$C_2F_4$-Cyc-PheFF-$CF_2$O-PheFF-$R^2$ | Iv |
| $R^1$-Cyc-$C_2F_4$-Cyc-$CF_2$O-Phe-Cyc-$R^2$ | Iw |

Of these, particular preference is given to the compounds of the sub-formulae Ia, Ib and Ic.

In the compounds of the formulae above and below, $R^2$ is preferably F, CN, $OCF_3$, $OCHF_2$, $CF_3$, $OCHFCF_3$, $OC_2F_5$ or $OCF_2CHFCF_3$, straight-chain alkyl or alkoxy.

$R^1$ is preferably straight-chain unsubstituted alkyl, alkoxy, alkenyloxy or alkenyl having up to 10 carbon atoms.

$A^2$ is preferably Phe, PheF, PheFF, Cyc or Che, furthermore Pyr or Dio, Dec or Nap. The compounds of the formula I preferably contain not more than one of the radicals Bi, Pyd, Pyr, Dio, Dit, Nap or Dec.

Preference is also given to all compounds of the formula I and of all sub-formulae in which $A^1$ is a monosubstituted or disubstituted 1,4-phenylene. These are, in particular, 2-fluoro-1,4-phenylene, 3-fluoro-1,4-phenylene, 2,3-difluoro-1,4-phenylene and 2,6-difluoro-1,4-phenylene.

Preferred smaller groups of compounds of the formula I are those of the sub-formulae I1 to I24:

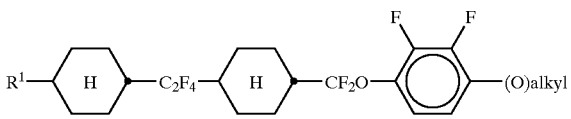

I1

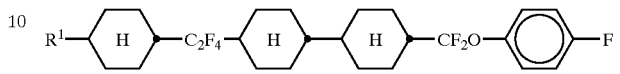

I2

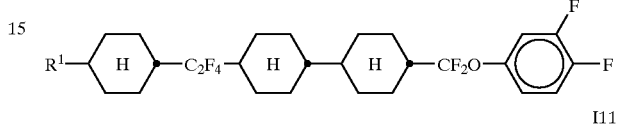

I3

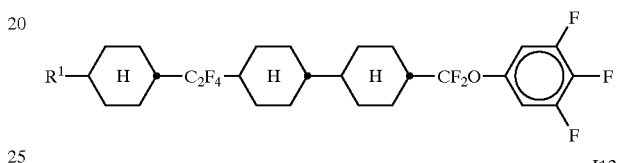

I4

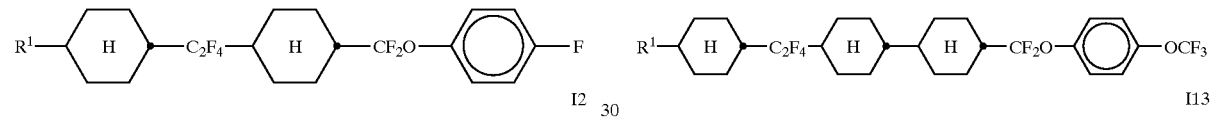

I5

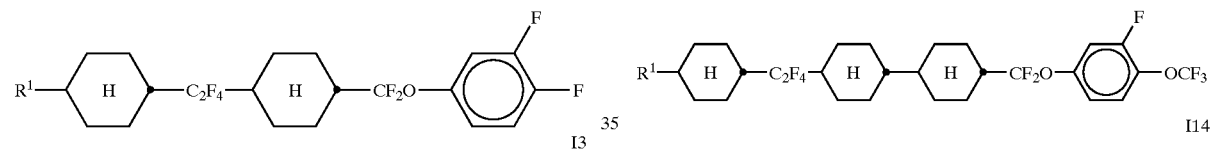

I6

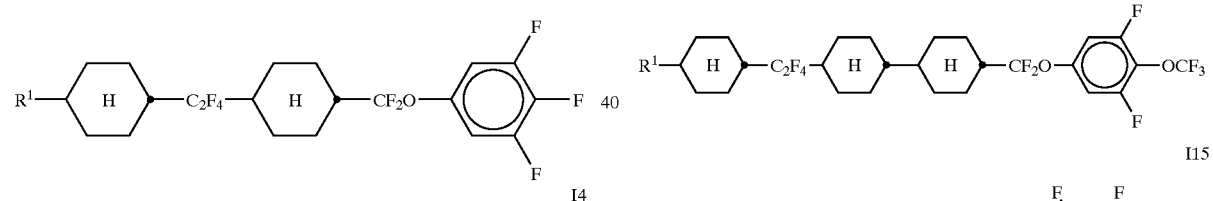

I7

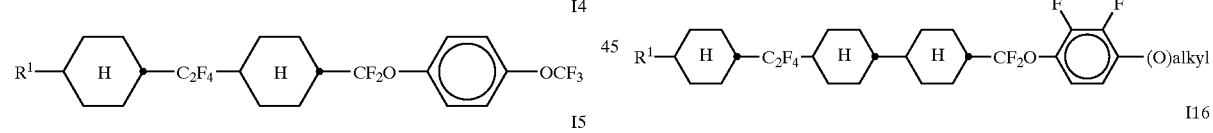

I8

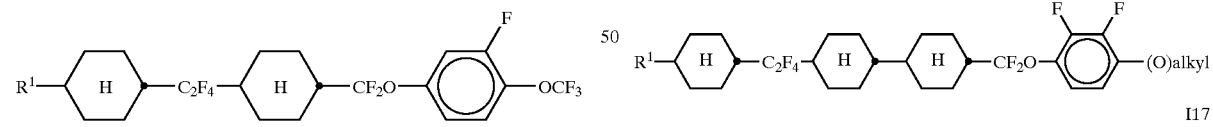

I9

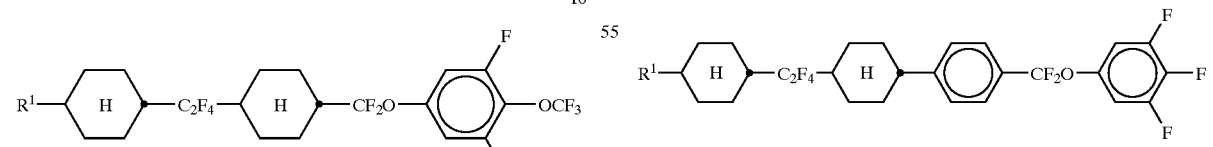

I10

I11

I12

I13

I14

I15

I16

I17

I18

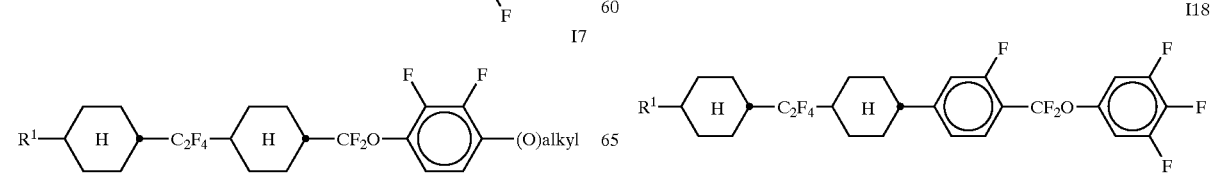

-continued

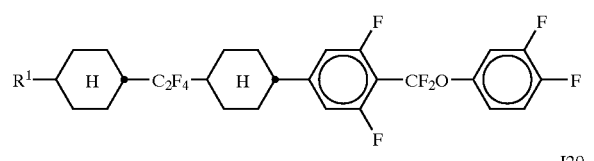
I19

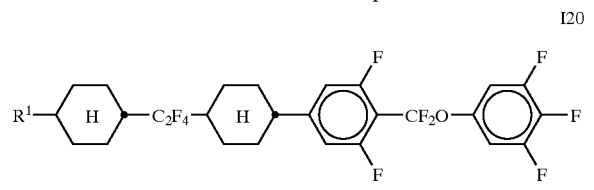
I20

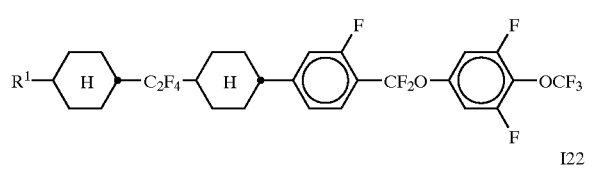
I21

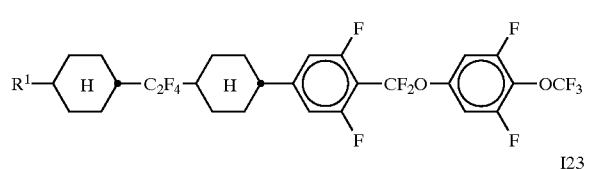
I22

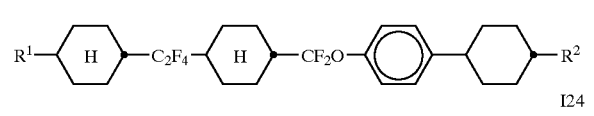
I23

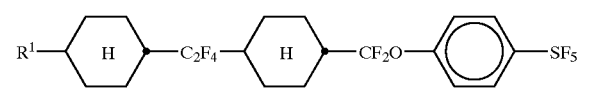
I24

In which $R^1$ is as defined in claim 1, and "alkyl" is a straight-chain or branched alkyl radical having 1–9 carbon atoms.

The compounds of the formula I are prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants which are known per se, but are not mentioned here in greater detail.

The compounds according to the invention can be prepared, for example, as follows:

Scheme 1

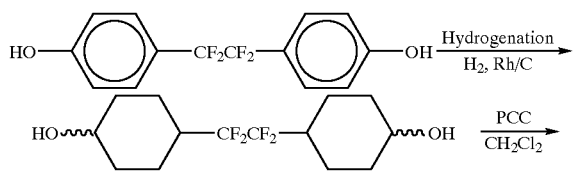

-continued

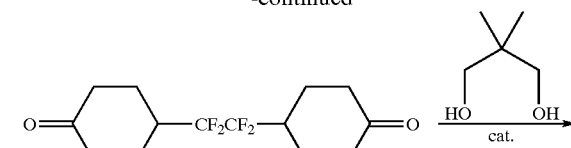

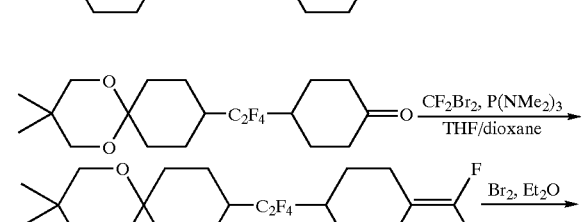

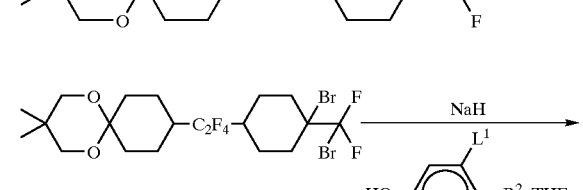

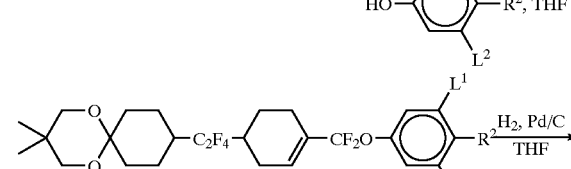

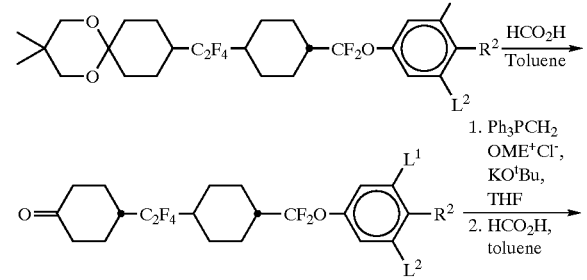

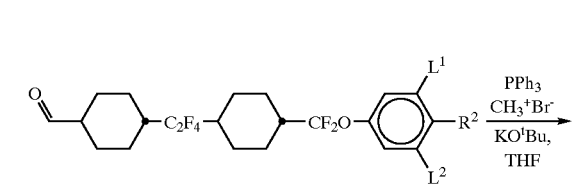

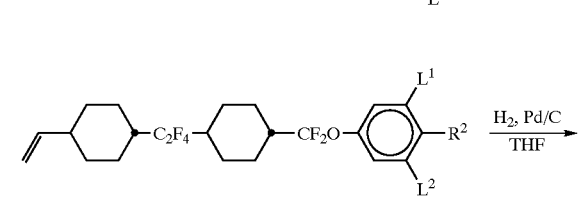

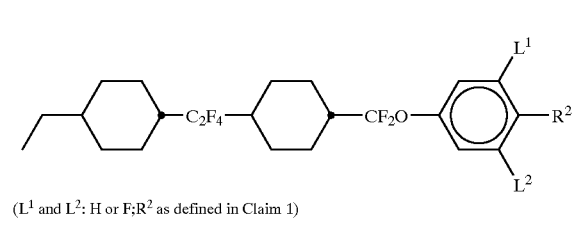

($L^1$ and $L^2$: H or F; $R^2$ as defined in Claim 1)

Scheme 2

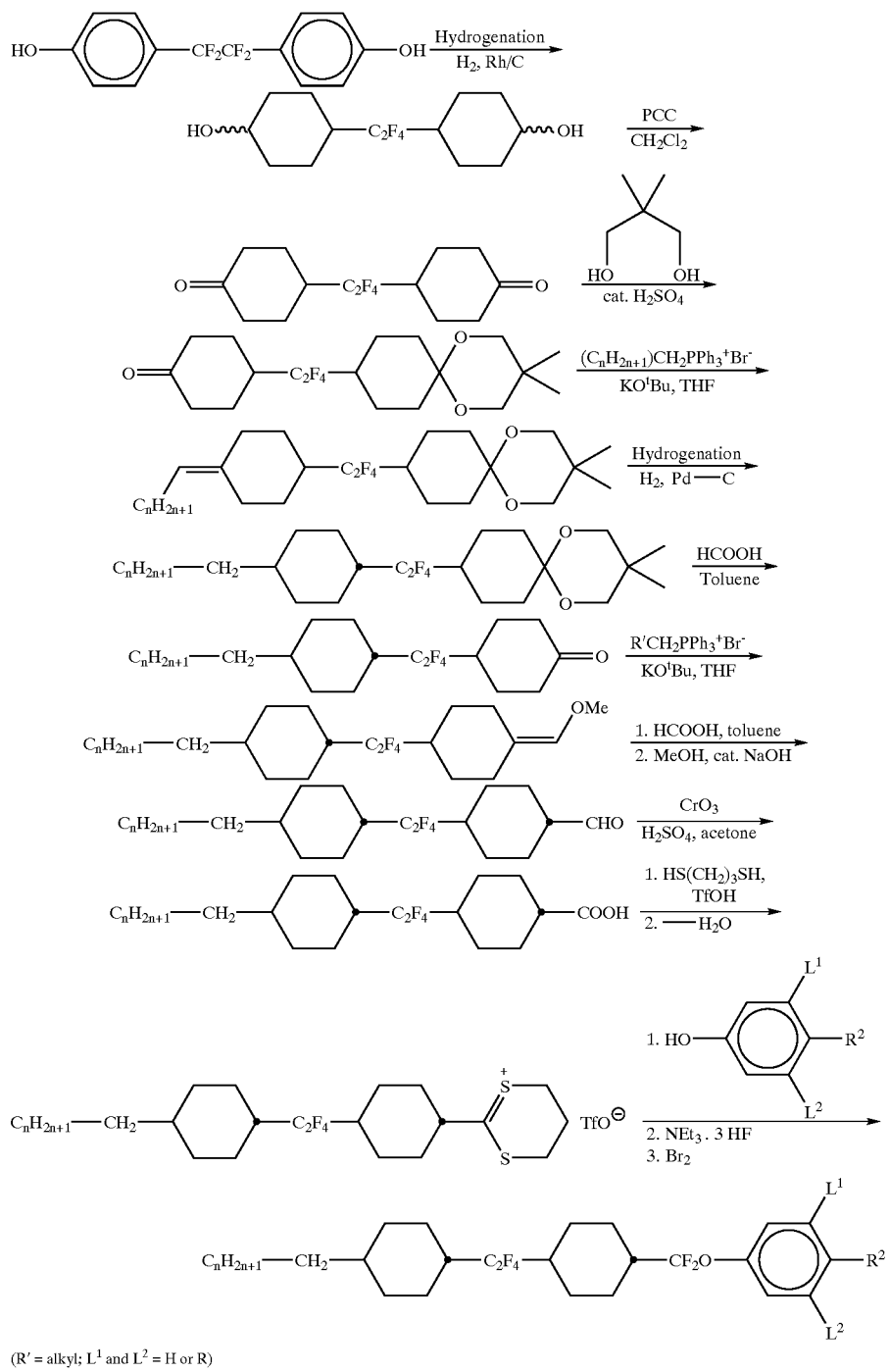

(R' = alkyl; $L^1$ and $L^2$ = H or R)

The invention also relates to electro-optical displays (in particular STN or MLC displays having two plane-parallel outer plates, which, together with a frame, form a cell, integrated non-linear elements for switching individual pixels on the outer plates, and a nematic liquid-crystal mixture of positive dielectric anisotropy and high specific resistance which is located in the cell) which contain media of this type, and to the use of these media for electro-optical purposes.

The liquid-crystal mixtures according to the invention enable a significant widening of the available parameter latitude.

The achievable combinations of clearing point, viscosity at low temperature, thermal and UV stability and dielectric anisotropy are far superior to previous materials from the prior art.

The requirement for a high clearing point, a nematic phase at low temperature and a high $\Delta\varepsilon$ has hitherto only been achieved to an inadequate extent. Although liquid-crystal mixtures such as, for example, MLC-6476 and MLC-6625 (Merck KgaA, Darmstadt, German) have comparable clearing points and low-temperature stabilities, they have, however, relatively low Δn values and also higher threshold voltages of about ≧1.7 V.

Other mixture systems have comparable viscosities and Δ∈ values, but only have clearing points in the region of 60° C.

The liquid-crystal mixtures according to the invention, while retaining the nematic phase down to −20° C. and preferably down to −30° C., particularly preferably down to −40° C., enable clearing points above 80° C., preferably above 90° C., particularly preferably above 100° C., simultaneously dielectric anisotropy values Δ∈ of ≧4, preferably ≧6, and a high value for the specific resistance to be achieved, enabling excellent STN and MLC displays to be obtained. In particular, the mixtures are characterised by low operating voltages. The TN thresholds are below 1.5 V, preferably below 1.3 V.

It goes without saying that, through a suitable choice of the components of the mixtures according to the invention, it is also possible for higher clearing points (for example above 110°) to be achieved at a higher threshold voltage or lower clearing points to be achieved at lower threshold voltages with retention of the other advantageous properties. At viscosities correspondingly increased only slightly, it is likewise possible to obtain mixtures having greater Δ∈ and thus lower thresholds. The MLC displays according to the invention preferably operate at the first Gooch and Tarry transmission minimum [C. H. Gooch and H. A. Tarry, Electron. Lett. 10, 2–4, 1974; C. H. Gooch and H. A. Tarry, Appl. Phys., Vol. 8, 1575–1584, 1975] are used, where, besides particularly favourable electro-optical properties, such as, for example, high steepness of the characteristic line and low angle dependence of the contrast (German Patent 30 22 818), a lower dielectric anisotropy is sufficient at the same threshold voltage as in an analogous display at the second minimum. This enables significantly higher specific resistances to be achieved using the mixtures according to the invention at the first minimum than in the case of mixtures comprising cyano compounds. Through a suitable choice of the individual components and their proportions by weight, the person skilled in the art is able to set the birefringence necessary for a pre-specified layer thickness of the MLC display using simple routine methods.

The flow viscosity $v_{20}$ at 20° C. is preferably <60 mm$^2$·s$^{-1}$, particularly preferably <50 mm$^2$·s$^{-1}$. The nematic phase range is preferably at least 90°, in particular at least 100°. This range preferably extends at least from −30° to +80°.

Measurements of the capacity holding ratio (HR) [S. Matsumoto et al., Liquid Crystals 5, 1320 (1989); K. Niwa et al., Proc. SID Conference, San Francisco, June 1984, p. 304 (1984); G. Weber et al., Liquid Crystals 5, 1381 (1989)] have shown that mixtures according to the invention comprising compounds of the formula I exhibit a significantly smaller decrease in the HR with increasing temperature than, for example, analogous mixtures comprising cyanophenyl-cyclohexanes of the formula

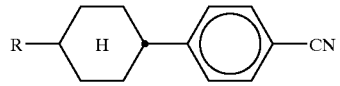

or esters of the formula

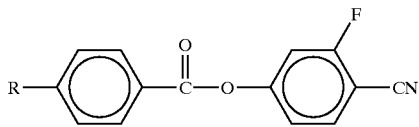

instead of the compounds of the formula I.

The UV stability of the mixtures according to the invention is also considerably better, i.e. they exhibit a significantly smaller decrease in the HR on exposure to UV.

The media according to the invention are preferably based on a plurality of (preferably two, three or more) compounds of the formula I, i.e. the proportion of these compounds is 5–95%, preferably 10–60% and particularly preferably in the range 15–40%.

The individual compounds of the formulae I to IX and their sub-formulae which can be used in the media according to the invention are either known or they can be prepared analogously to the known compounds.

Preferred embodiments are indicated below:

The medium preferably comprises one, two or three homologous compounds of the formula I, where each homologue is present in the mixture in a maximum proportion of 10%.

The medium comprises compounds of the formula I in which $R^1$ is preferably ethyl and/or propyl, furthermore butyl, pentyl, hexyl and heptyl. Compounds of the formula I having short side chains $R^1$ have a positive effect on the elastic constants, in particular $K_1$, and result in mixtures having particularly low threshold voltages.

Medium additionally comprises one or more compounds selected from the group consisting of the general formulae II to IX:

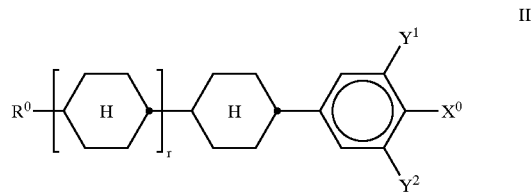

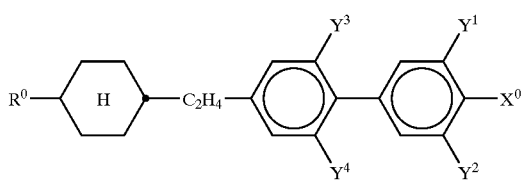

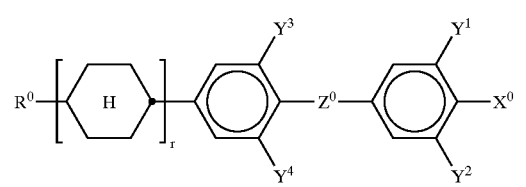

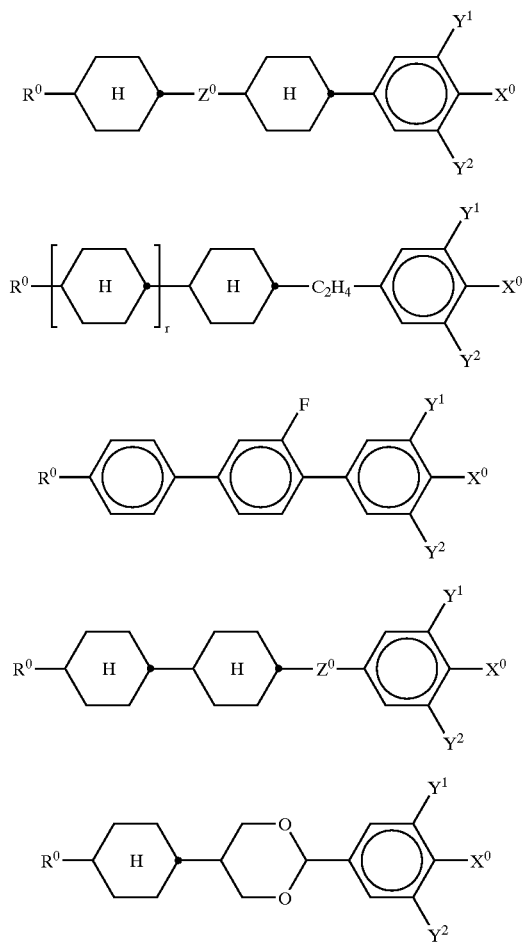

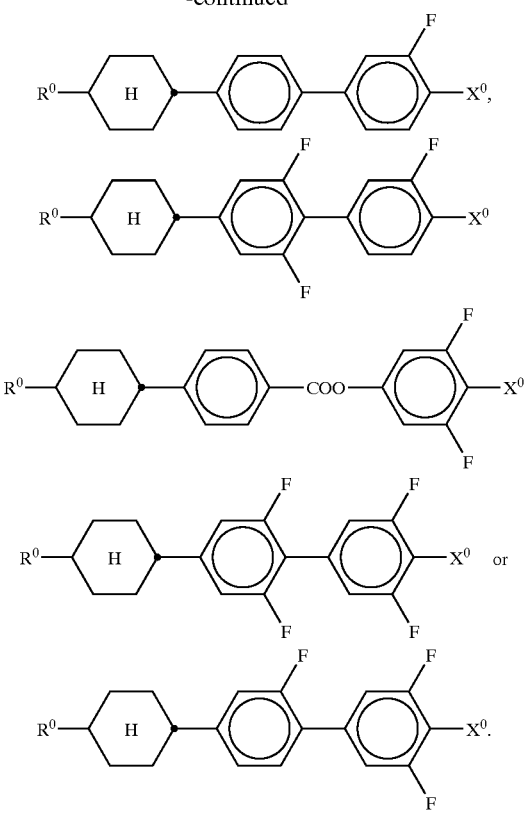

In which the individual radicals have the following meanings.

$R^0$ is n-alkyl, oxaalkyl, fluoroalkyl, alkenyloxy or alkenyl, each having up to 9 carbon atoms,
$X^0$ is F, Cl, halogenated alkyl, halogenated alkenyl, halogenated alkenyloxy or halogenated alkoxy having up to 7 carbon atoms,
$Z^0$ is —CH=CH—, —C₂H₄—, —C₂F₄—, —CF=CF—, —CF₂O—, —OCF₂— or —COO—,
$Y^1, Y^2$, $Y^3$ and $Y^4$ are each, independently of one another, H or F, and
r is 0 or 1.

The compound of the formula IV is preferably

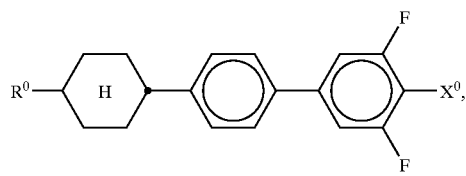

Medium additionally comprises one or more compounds of the formulae

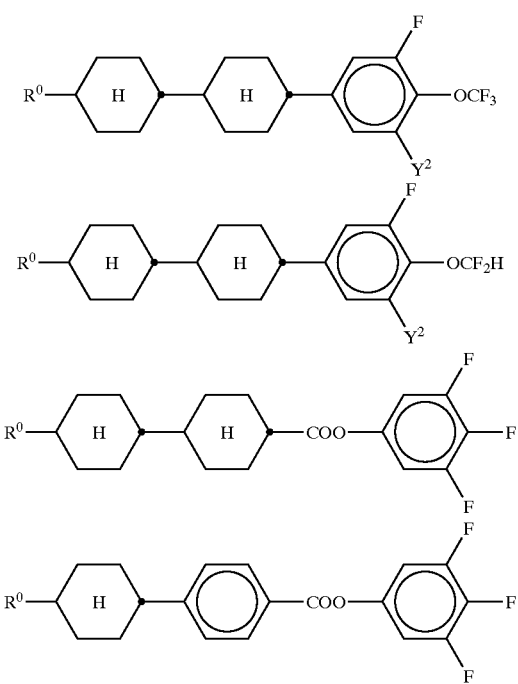

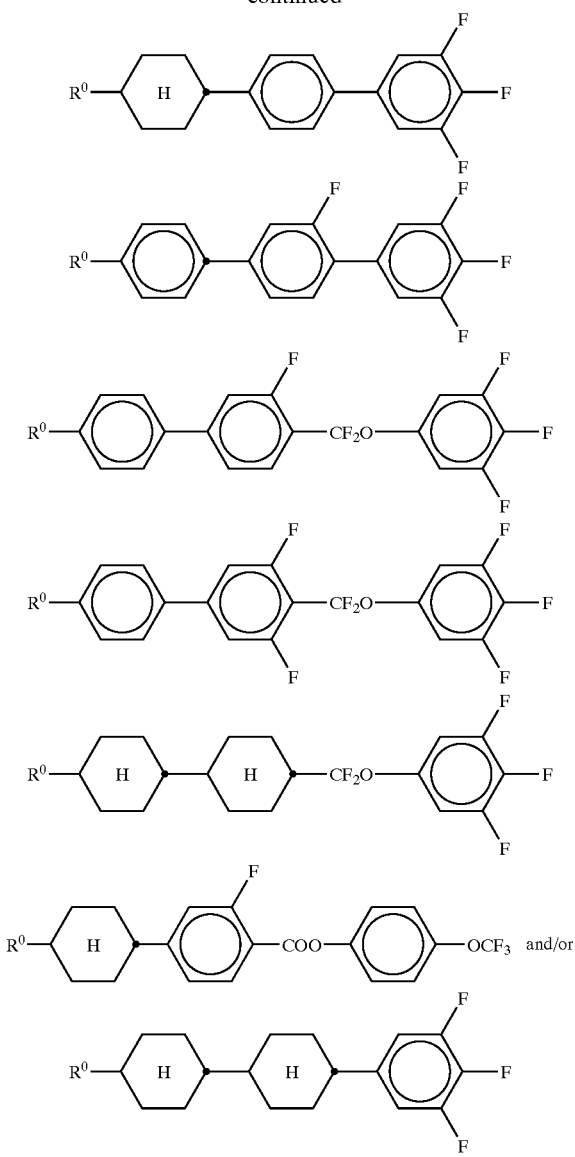
In which $R^0$ and $Y^2$ are as defined above.
The medium preferably comprises one, two or three, furthermore four, homologues of the compounds selected from the group consisting of H1 to H16 (n=1–7):
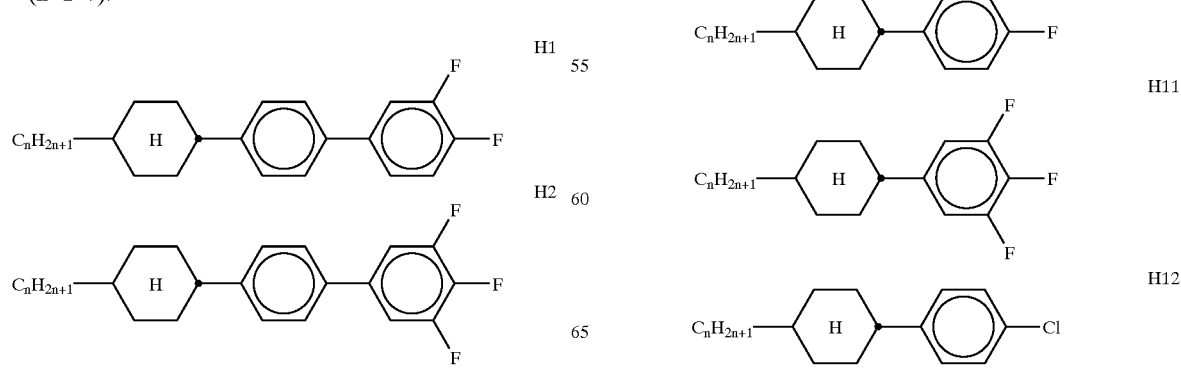

H13

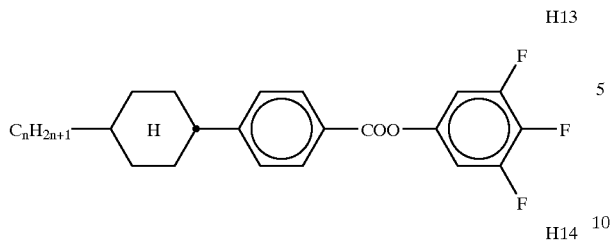

H14

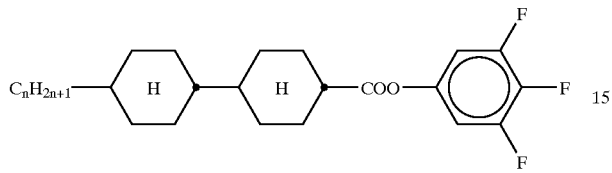

H15

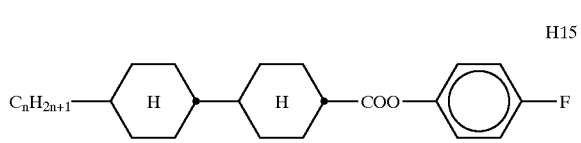

H16

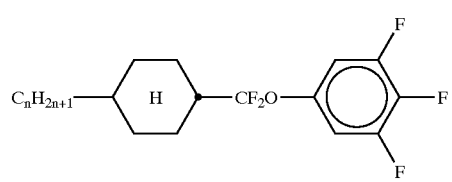

The medium additionally comprises one or more dioxanes of the formulae DI and/or DII:

DI

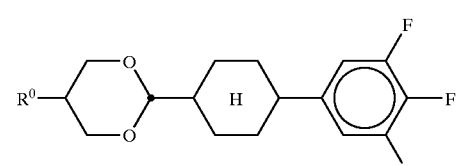

DII

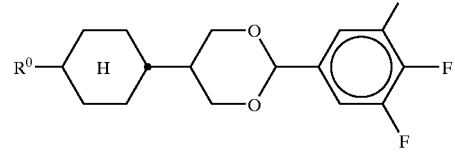

In which $R^0$ is as defined in claim 7. $R^0$ in the compounds of the formulae DI and DII is preferably straight-chain alkyl or alkenyl having up to 7 carbon atoms.

The medium additionally comprises one or more compounds selected from the group consisting of the general formulae X to XV:

X

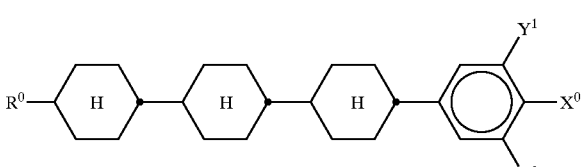

XI

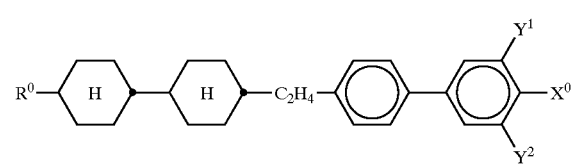

XII

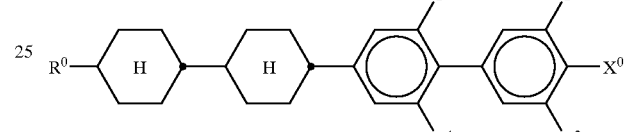

XIII

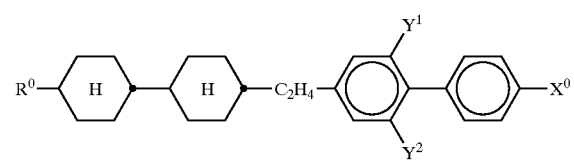

XIV

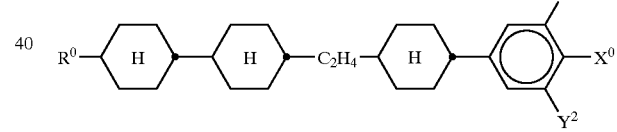

XV

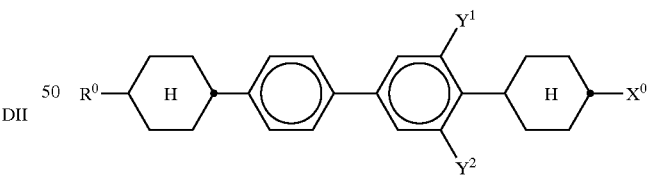

in which $R^0$, $X^0$, $Y^1$, $Y^2$, $Y^3$ and $Y^4$ are each, independently of one another, as defined in claim 7, $X^0$ is preferably F, Cl, $CF_3$, $OCF_3$ or $OCHF_2$. $R^0$ is preferably alkyl, oxaalkyl, fluoroalkyl, alkenyl or alkenyloxy.

The proportion of compounds of the formulae I to IX together in the mixture as a whole is at least 50% by weight.

The proportion of compounds of the formula I in the mixture as a whole is from 5 to 50% by weight.

The proportion of compounds of the formulae II to IX in the mixture as a whole is from 30 to 70% by weight.

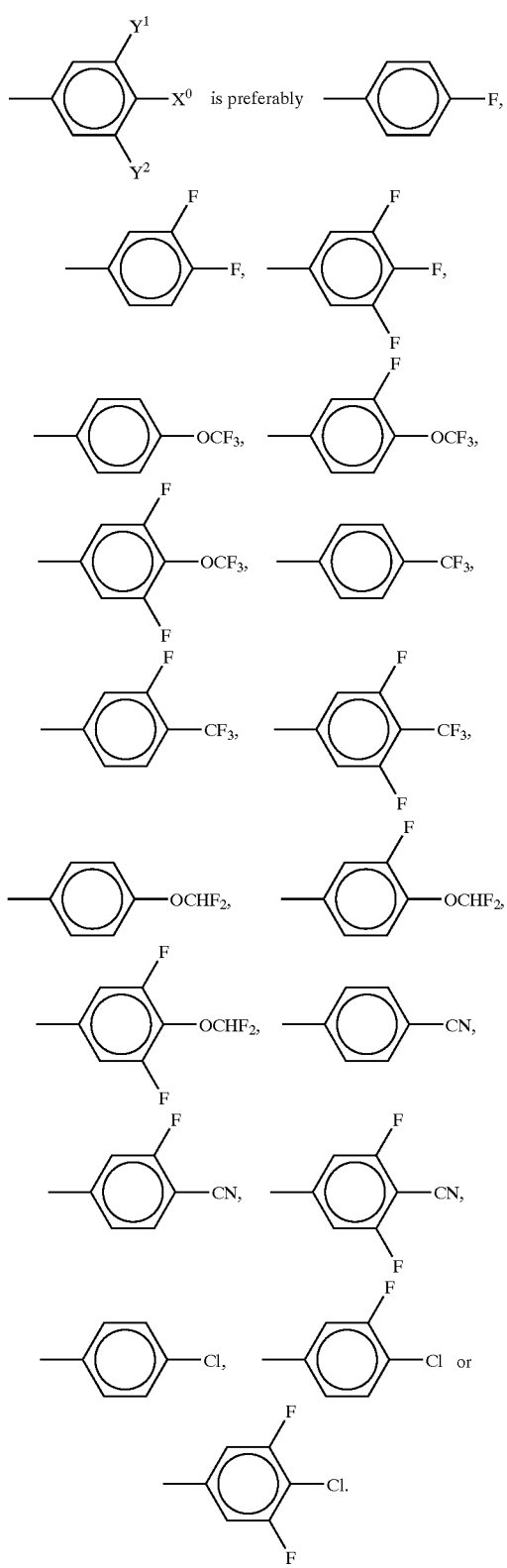

The medium comprises compounds of the formulae II, III, IV, V, VI, VII, VIII and/or IX.

$R^0$ is straight-chain alkyl or alkenyl having from 2 to 7 carbon atoms.

The medium essentially consists of compounds of the formulae I to XV.

The medium comprises further compounds, preferably selected from the following group consisting of the general formulae XVI to XIX:

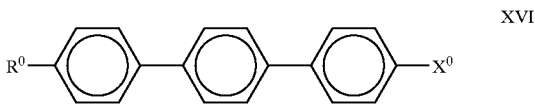

XVI

XVII

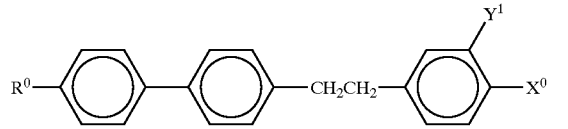

XVIII

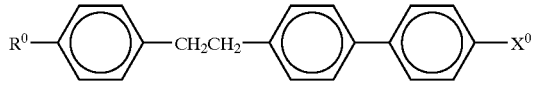

XIX

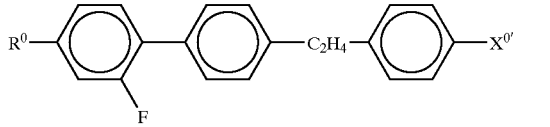

($X^{0'}$ = F or Cl)

in which $R^0$ and $X^0$ are as defined above, and the 1,4-phenylene rings may be substituted by CN, chorine or fluorine. The 1,4-phenylene rings are preferably monosubstituted or polysubstituted by fluorine atoms.

The medium comprises further compounds, preferably selected from the following group consisting of the formulae RI to RX:

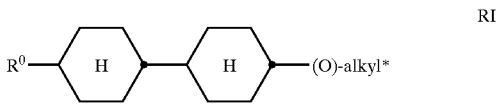

RI

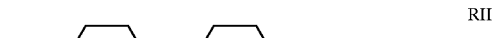

RII

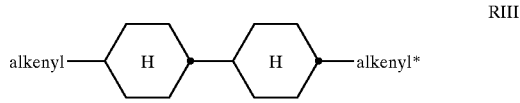

RIII

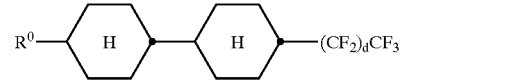

RIV

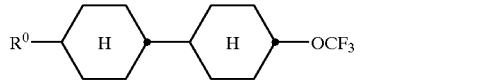

RV

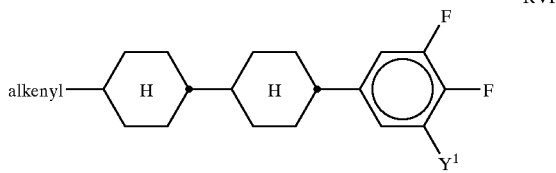

RVI

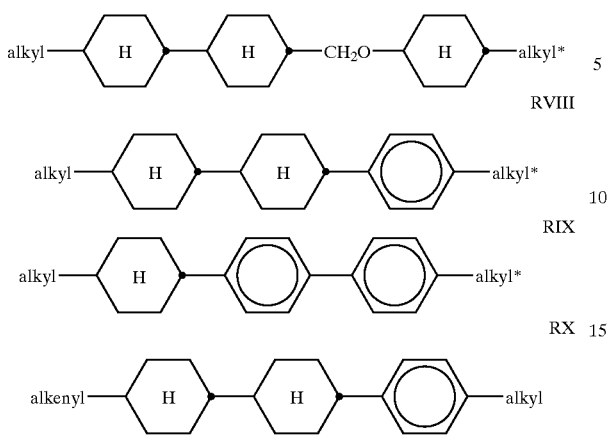

in which
R⁰ is n-alkyl, oxaalkyl, fluoroalkyl, alkenyloxy or alkenyl, each having up to 9 carbon atoms,
d is 0, 1 or 2,
$Y^1$ is H or F,
alkyl or
alkyl* are each, independently of one another, a straight-chain or branched alkyl radical having 1–9 carbon atoms,
alkenyl or
alkenyl* are each, independently of one another, a straight-chain or branched alkenyl radical having up to 9 carbon atoms.

The medium preferably comprises one or more compounds of the formulae

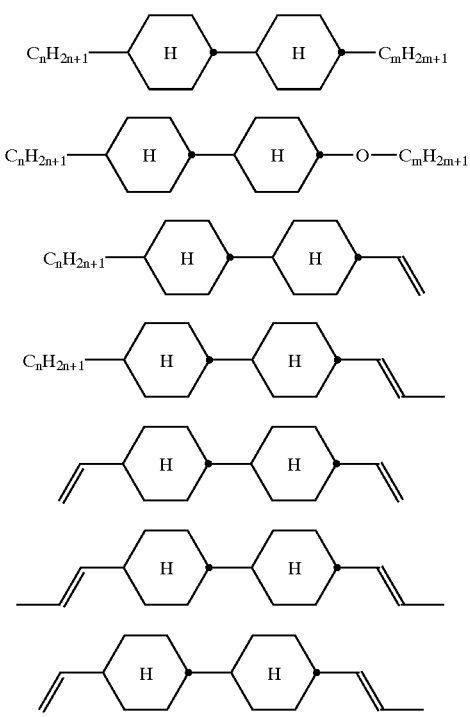

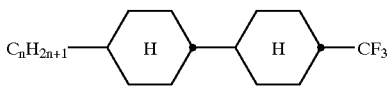

in which n and m are an integer from 1–9.

The I: (II+III+IV+V+VI+VII+VIII+IX) weight ratio is preferably from 1:10 to 10:1.

Medium essentially consists of compounds selected from the group consisting of the general formulae I to XV.

It has been found that even a relatively small proportion of compounds of the formula I mixed with conventional liquid-crystal materials, but in particular with one or more compounds of the formulae II, III, IV, V, VI, VII, VIII and/or IX, results in a significant lowering of the threshold voltage and in low birefringence values, with broad nematic phases with low smectic-nematic transition temperatures being observed at the same time, improving the shelf life. The compounds of the formulae I to IX are colourless, stable and readily miscible with one another and with other liquid-crystalline materials.

The term "alkyl" or "alkyl*" covers straight-chain and branched alkyl groups having 1–9 carbon atoms, in particular the straight-chain groups methyl, ethyl, propyl, butyl, pentyl, hexyl and heptyl. Groups having 2–5 carbon atoms are generally preferred.

The term "alkenyl" or "alkenyl*" covers straight-chain and branched alkenyl groups having up to 9 carbon atoms, in particular the straight-chain groups. Preferred alkenyl groups are $C_2$–$C_7$-1E-alkenyl, $C_4$–$C_7$-3E-alkenyl, $C_5$–$C_7$-4-alkenyl, $C_6$–$C_7$-5-alkenyl and $C_7$-6-alkenyl, in particular $C_2$–$C_7$-1E-alkenyl, $C_4$–$C_7$-3E-alkenyl and $C_5$–$C_7$-4-alkenyl. Examples of particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 carbon atoms are generally preferred.

The term "fluoroalkyl" preferably covers straight-chain groups having a terminal fluorine, i.e. fluoromethyl, 2-fluoroethyl, 3-fluoropropyl, 4-fluorobutyl, 5-fluoropentyl, 6-fluorohexyl and 7-fluoroheptyl. However, other positions of the fluorine are not excluded.

The term "oxaalkyl" preferably covers straight-chain radicals of the formula $C_nH_{2n+1}$—O—$(CH_2)_m$, in which n and m are each, independently of one another, from 1 to 6. n is preferably=1 and m is preferably from 1 to 6.

Through a suitable choice of the meanings of R⁰ and X⁰, the addressing times, the threshold voltage, the steepness of the transmission characteristic lines, etc., can be modified in the desired manner. For example, 1E-alkenyl radicals, 3E-alkenyl radicals, 2E-alkenyloxy radicals and the like generally result in shorter addressing times, improved nematic tendencies and a higher ratio of the elastic constants $k_{33}$ (bend) and $k_{11}$ (splay) compared with alkyl or alkoxy radicals. 4-alkenyl radicals, 3-alkenyl radicals and the like generally give lower threshold voltages and smaller values of $k_{33}/k_{11}$ compared with alkyl and alkoxy radicals.

A —$CH_2CH_2$— group in $Z^1$ generally results in higher values of $k_{33}/k_{11}$ compared with a single covalent bond. Higher values of $k_{33}/k_{11}$ facilitate, for example, flatter transmission characteristic lines in TN cells with a 90° twist (in order to achieve grey shades) and steeper transmission characteristic lines in STN, SBE and OMI cells (greater multiplexability), and vice versa.

The optimum mixing ratio of the compounds of the formulae I and II+III+IV+V+VI+VII+VII+IX depends substantially on the desired properties, on the choice of the components of the formulae I, II, III, IV, V, VI, VII, VIII and/or IX, and the choice of any other components that may be present. Suitable mixing ratios within the range given above can easily be determined from case to case.

The total amount of compounds of the formulae I to XV in is not crucial. The mixtures can therefore comprise one or more further components for the purposes of optimising various properties. However, the observed effect on the addressing times and the threshold voltage is generally greater, the higher the total concentration of compounds of the formulae I to XV.

In a particularly preferred embodiment, the media according to the invention comprise compounds of the formulae II to IX (preferably II and/or III) in which $X^0$ is $OCF_3$, $OCHF_2$, F, $OCH=CF_2$, $OCF=CF_2$, $OCF_2CHFCF_3$ or $OCF_2-CF_2H$. A favourable synergistic effect with the compounds of the formula I results in particularly advantageous properties.

The mixtures according to the invention of low optical anisotropy ($\Delta n \leq 0.09$) are particularly suitable for reflective displays. Low $V_{th}$ mixtures are particularly suitable for 3.3 V drivers and 4 V and 5 V drivers. Ester-free mixtures are preferred for the last-mentioned applications. The mixtures according to the invention result in an improvement in reliability (image sticking, point defect, etc.) and are therefore also highly suitable for IPS applications.

The construction of the MLC display according to the invention from polarisers, electrode base plates and surface-treated electrodes corresponds to the conventional construction for displays of this type. The term "conventional construction" is broadly drawn here and also covers all derivatives and modifications of the MLC display, in particular including matrix display elements based on poly-Si TFT or MIM.

A significant difference between the displays according to the invention and the conventional displays based on the twisted nematic cell consists, however, in the choice of the liquid-crystal parameters of the liquid-crystal layer.

The liquid-crystal mixtures which can be used in accordance with the invention are prepared in a manner conventional per se. In general, the desired amount of the components used in the lesser amount is dissolved in the components making up the principal constituent, advantageously at elevated temperature. It is also possible to mix solutions of the components in an organic solvent, for example in acetone, chloroform or methanol, and to remove the solvent again, for example by distillation, after thorough mixing.

The dielectrics may also comprise further additives known to the person skilled in the art and described in the literature. For example, 0–15% of pleochroic dyes or chiral dopants can be added.

C denotes a crystalline phase, S a smectic phase, $S_C$ a smectic C phase, N a nematic phase and I the isotropic phase.

$V_{10}$ denotes the voltage for 10% transmission (viewing angle perpendicular to the plate surface). $t_{on}$ denotes the switch-on time and $t_{off}$ the switch-off time at an operating voltage corresponding to 2 times the value of $V_{10}$. $\Delta n$ denotes the optical anisotropy and $n_o$ the refractive index. $\Delta\varepsilon$ denotes the dielectric anisotropy ($\Delta\varepsilon=\varepsilon_\parallel-\varepsilon_\perp$, where $\varepsilon_\parallel$ denotes the dielectric constant parallel to the longitudinal molecular axes and $\varepsilon_\perp$ denotes the dielectric constant perpendicular thereto). The electro-optical data were measured in a TN cell at the 1st minimum (i.e. at a d·$\Delta n$ value of 0.5) at 20° C., unless expressly stated otherwise. The optical data were measured at 20° C., unless expressly stated otherwise.

In the present application and in the examples below, the structures of the liquid-crystal compounds are indicated by means of acronyms, the transformation into chemical formulae taking place in accordance with Tables A and B below. All radicals $C_nH_{2n+1}$ and $C_mH_{2m+1}$ are straight-chain alkyl radicals having n and m carbon atoms respectively; n and m are in each case, independently of one another, 1, 2, 3, 4, 5, 6, 7, 8, 9, 10, 11, 12, 13, 14 or 15. The coding in Table B is self-evident. In Table A, only the acronym for the parent structure is indicated. In individual cases, the acronym for the parent structure is followed, separated by a dash, by a code for the substituents $R^1$, $R^2$, $L^1$ and $L^2$:

| Code for $R^1$, $R^2$, $L^1$, $L^2$ | $R^1$ | $R^2$ | $L^1$ | $L^2$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | H | F |
| nF | $C_nH_{2n+1}$ | F | H | H |
| nOF | $OC_nH_{2n+1}$ | F | H | H |
| nCl | $C_nH_{2n+1}$ | Cl | H | H |
| nF.F | $C_nH_{2n+1}$ | F | H | F |
| nF.F.F | $C_nH_{2n+1}$ | F | F | F |
| nCF$_3$ | $C_nH_{2n+1}$ | CF$_3$ | H | H |
| nOCF$_3$ | $C_nH_{2n+1}$ | OCF$_3$ | H | H |
| nOCF$_2$ | $C_nH_{2n+1}$ | OCHF$_2$ | H | H |
| nS | $C_nH_{2n+1}$ | NCS | H | H |
| rVsN | $C_rH_{2r+1}$—CH=CH—$C_sH_{2s}$— | CN | H | H |
| rEsN | $C_rH_{2r+1}$—O—$C_sH_{2s}$— | CN | H | H |
| nAm | $C_nH_{2n+1}$ | COOC$_m$H$_{2m+1}$ | H | H |
| nOCCF$_2$.F.F | $C_nH_{2n+1}$ | OCH$_2$CF$_2$H | F | F |

Preferred mixture components are shown in Tables A and B.

TABLE A

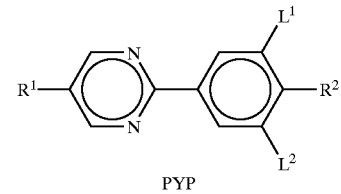

PYP

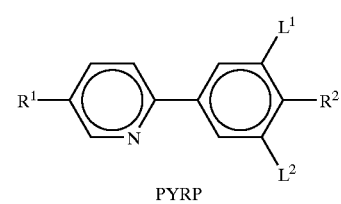

PYRP

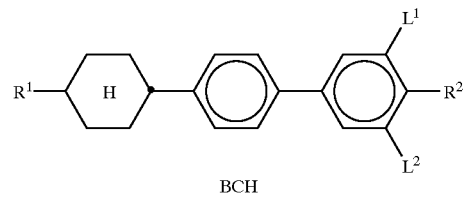

BCH

TABLE A-continued
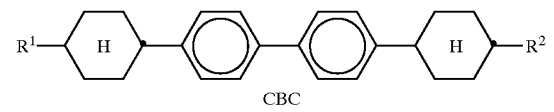
CBC
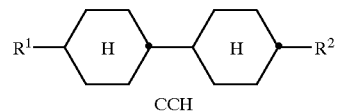
CCH
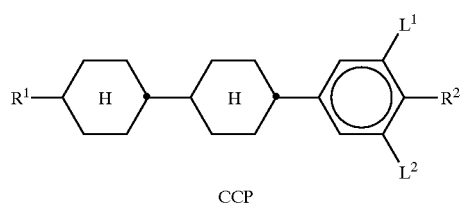
CCP
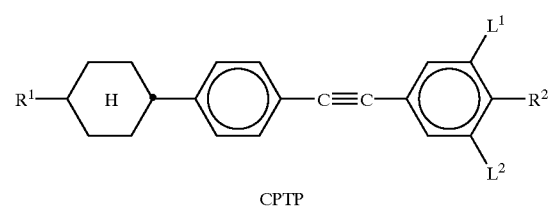
CPTP
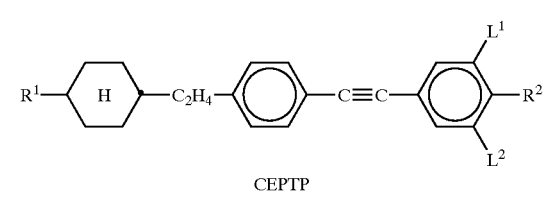
CEPTP
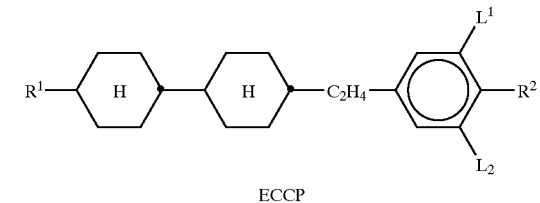
ECCP
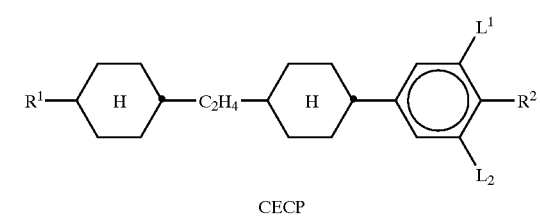
CECP
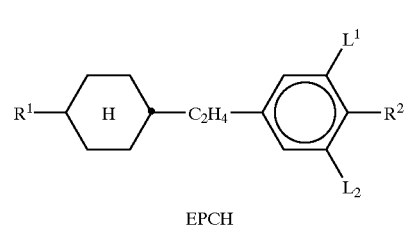
EPCH
TABLE A-continued
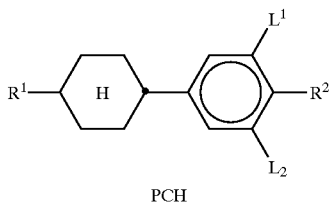
PCH
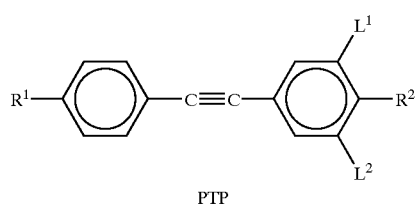
PTP
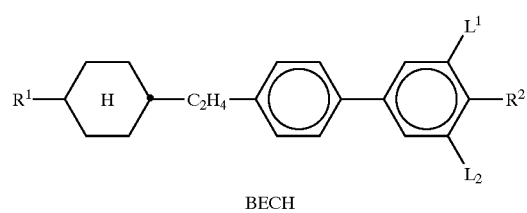
BECH
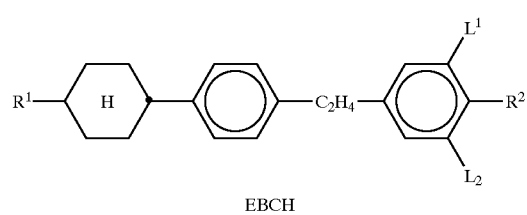
EBCH
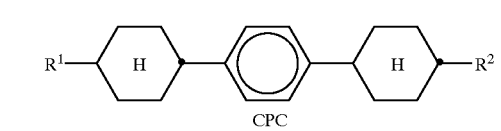
CPC
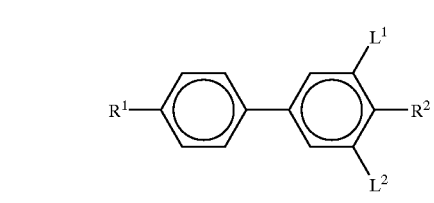
B
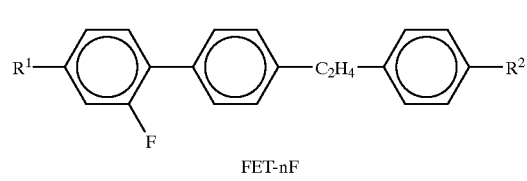
FET-nF
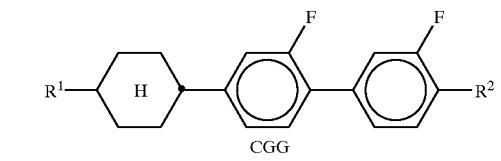
CGG

TABLE A-continued
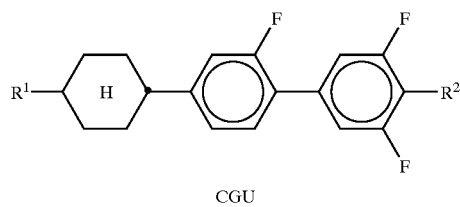
CGU
TABLE A-continued
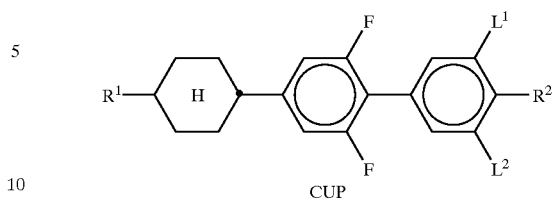
CUP
TABLE B
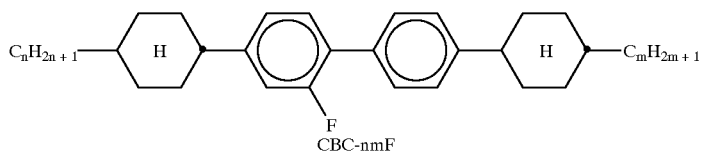
CBC-nmF
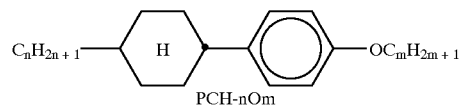
PCH-nOm
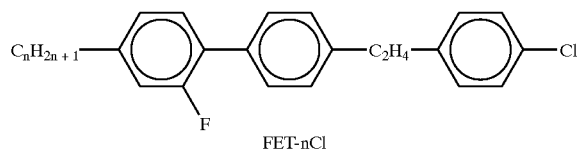
FET-nCl
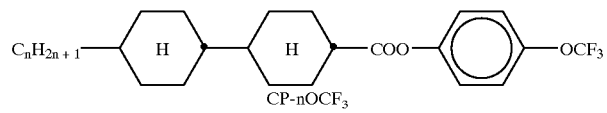
CP-nOCF$_3$
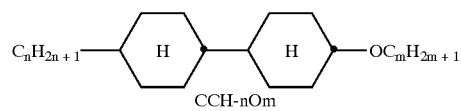
CCH-nOm
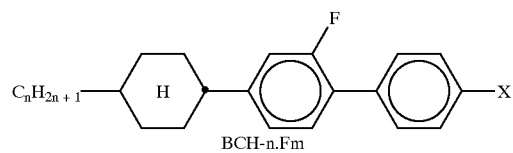
BCH-n.Fm
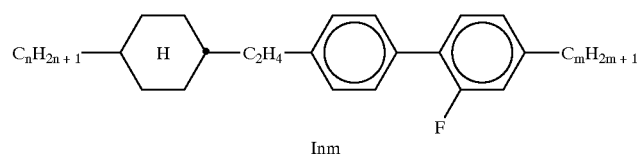
Inm
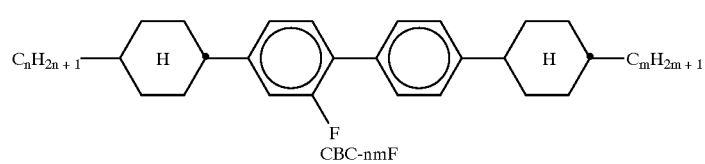
CBC-nmF
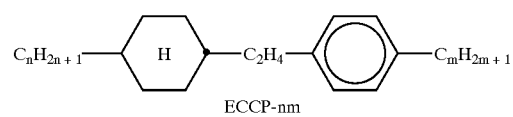
ECCP-nm TABLE B-continued
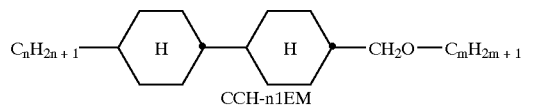
CCH-n1EM
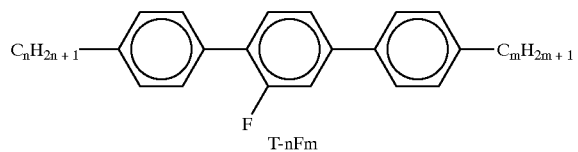
T-nFm
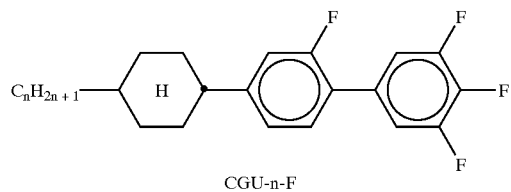
CGU-n-F
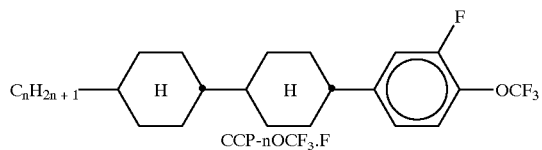
CCP-nOCF$_3$.F
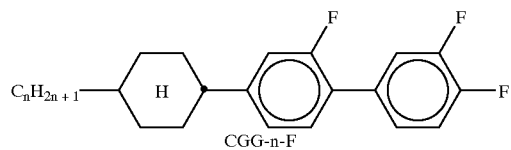
CGG-n-F
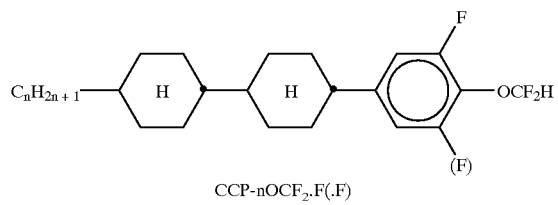
CCP-nOCF$_2$.F(.F)
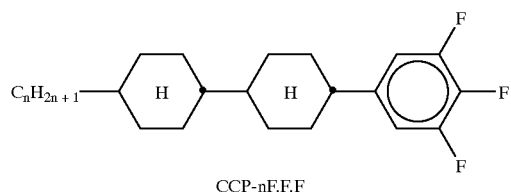
CCP-nF.F.F
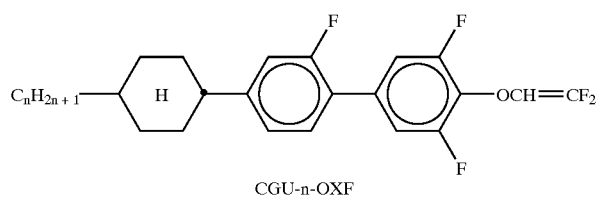
CGU-n-OXF
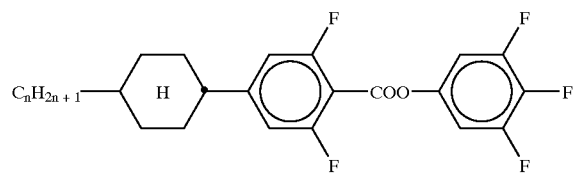

TABLE B-continued
CUZU-n-F
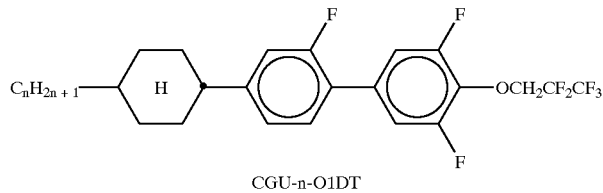
CGU-n-O1DT
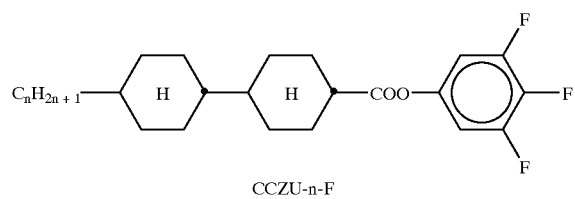
CCZU-n-F
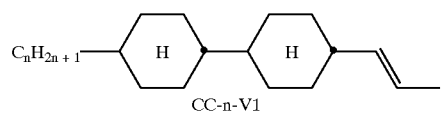
CC-n-V1
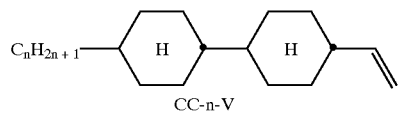
CC-n-V
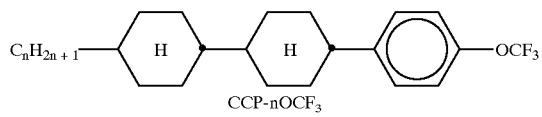
CCP-nOCF$_3$
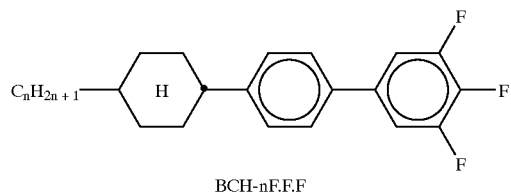
BCH-nF.F.F
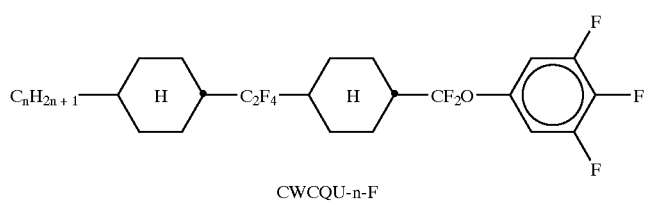
CWCQU-n-F
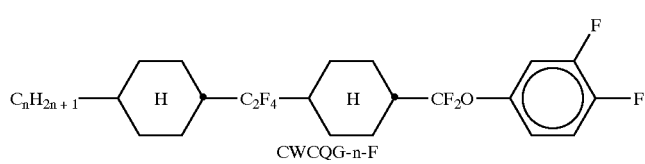
CWCQG-n-F
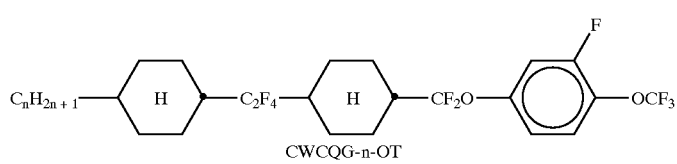
CWCQG-n-OT TABLE B-continued
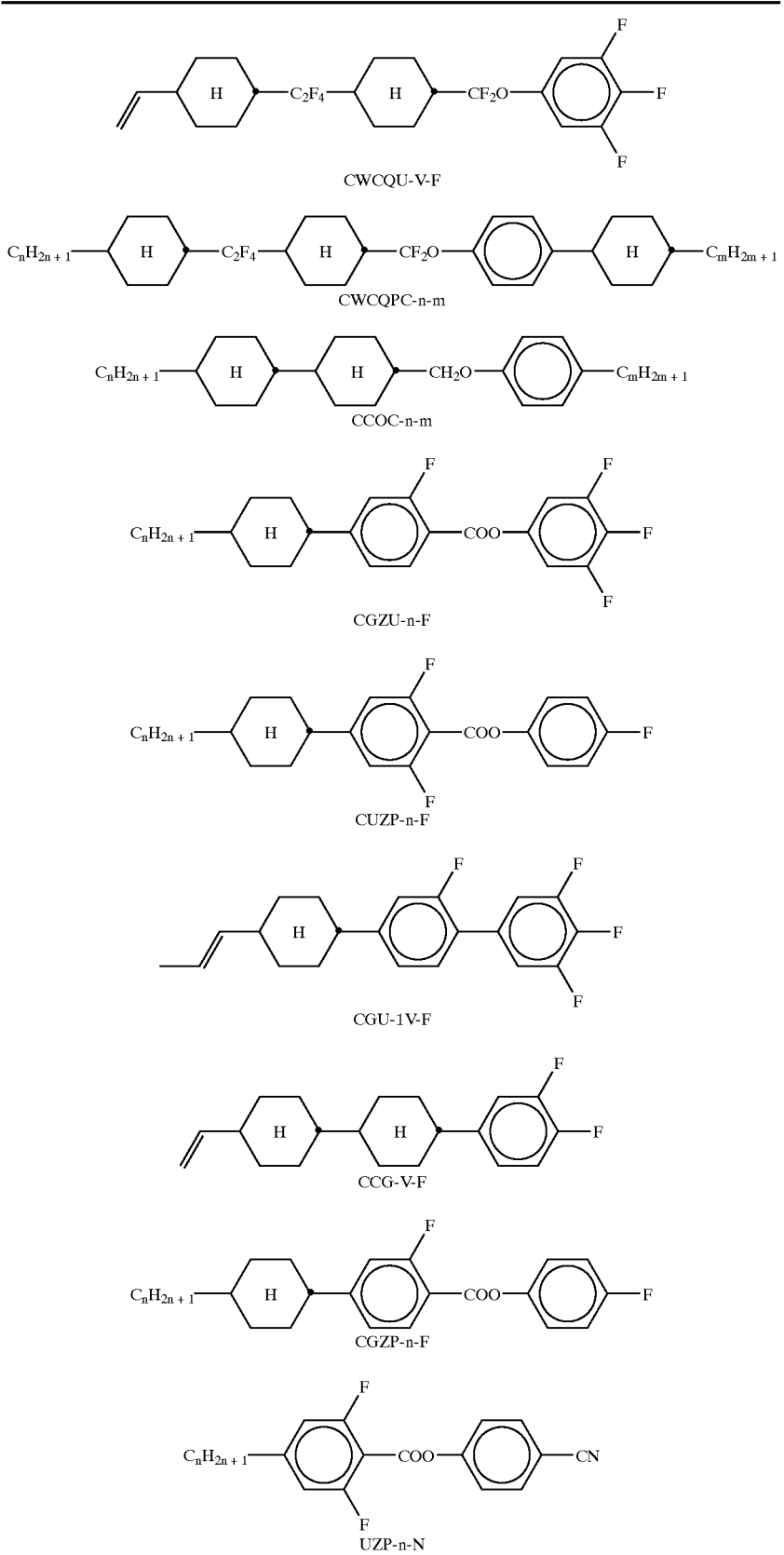

TABLE B-continued
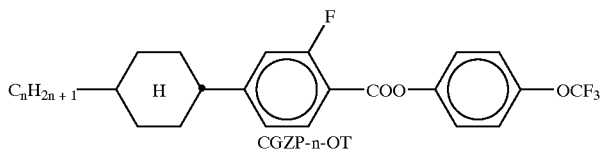
CGZP-n-OT
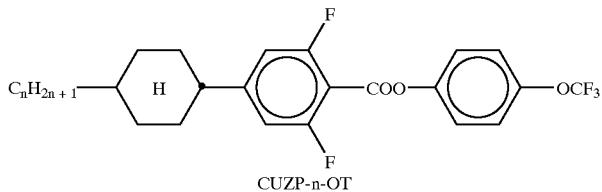
CUZP-n-OT
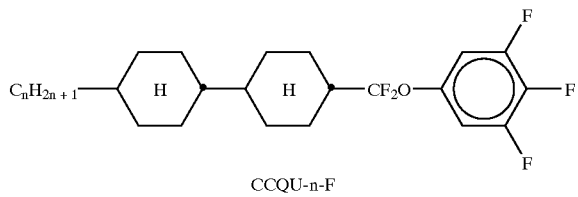
CCQU-n-F
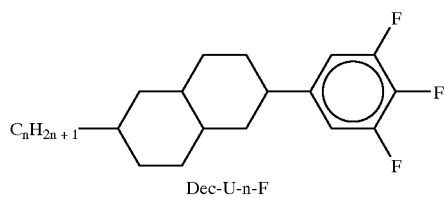
Dec-U-n-F
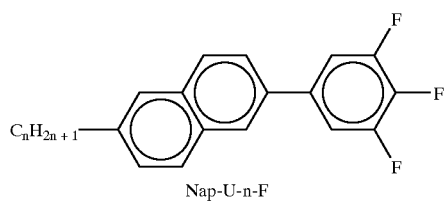
Nap-U-n-F
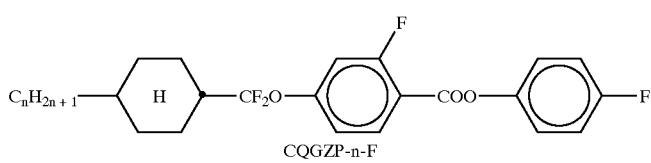
CQGZP-n-F
TABLE C
Table C indicates possible dopants which are generally added to the mixtures according to the invention.
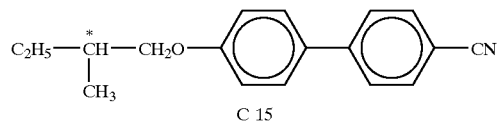
C 15
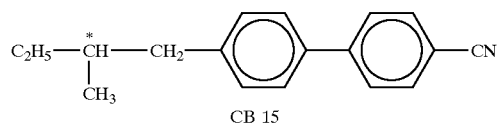
CB 15

TABLE C-continued
Table C indicates possible dopants which are generally added to the mixtures according to the invention.
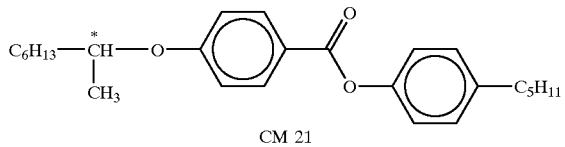
CM 21
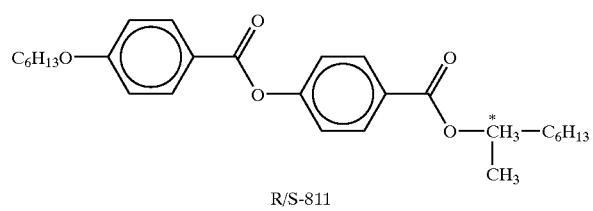
R/S-811
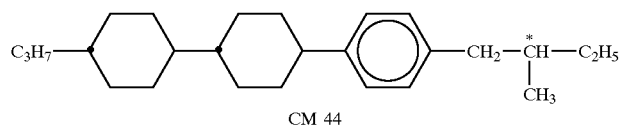
CM 44
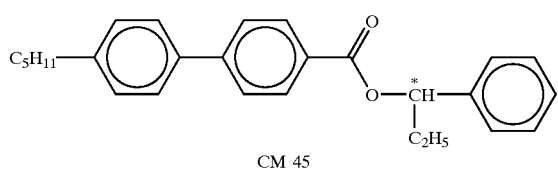
CM 45
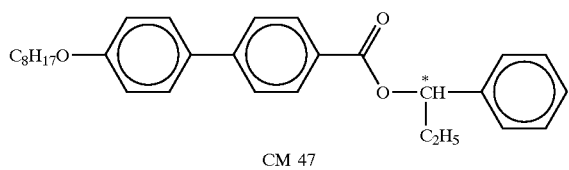
CM 47
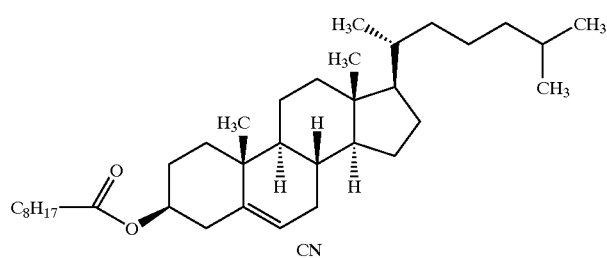
CN
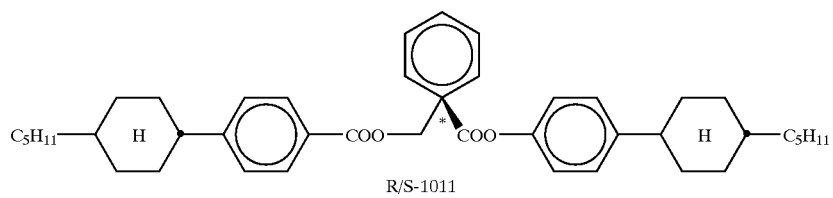
R/S-1011
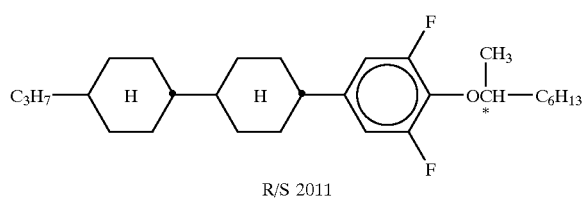
R/S 2011

TABLE C-continued
Table C indicates possible dopants which are generally added to the mixtures according to the invention.
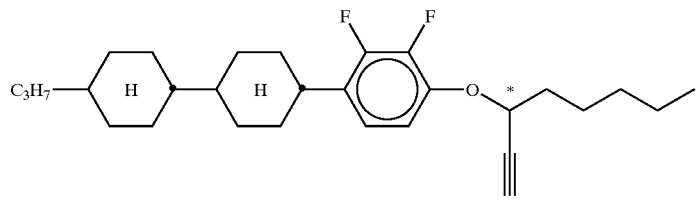
R/S-3011
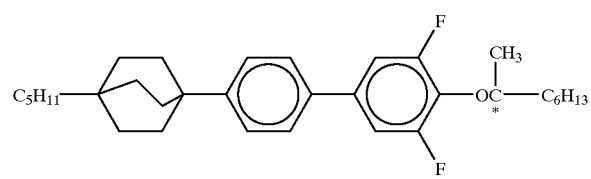
R/S-4011
TABLE D
Stabilisers which can be added, for example, to the mixtures according to the invention are indicated below.
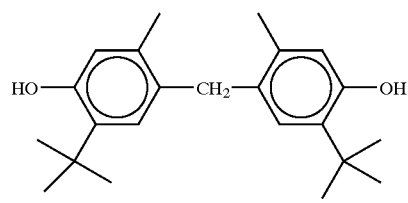
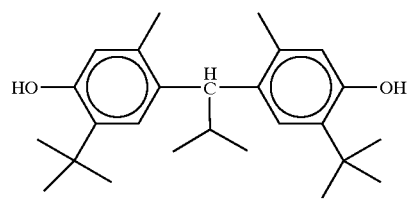
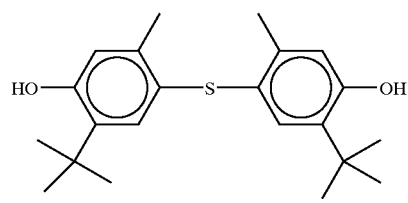
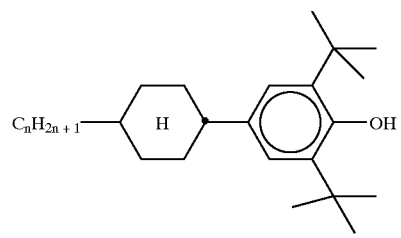

TABLE D-continued
Stabilisers which can be added, for example, to the mixtures according to the invention are indicated below.
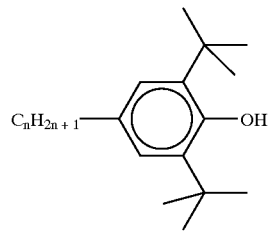
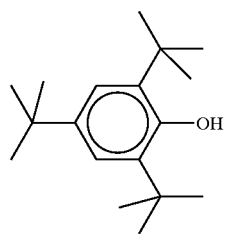
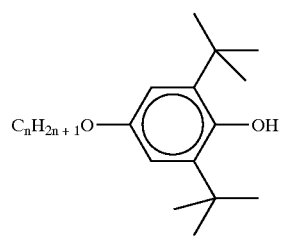
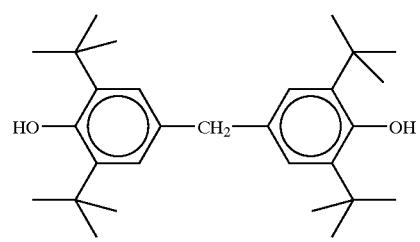
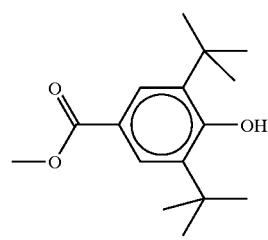
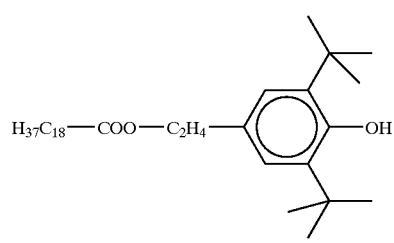

TABLE D-continued
Stabilisers which can be added, for example, to the mixtures according to the invention are indicated below.
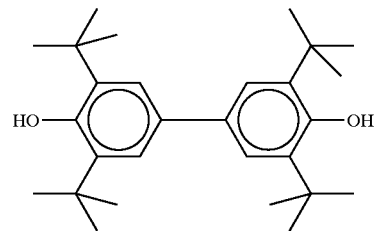
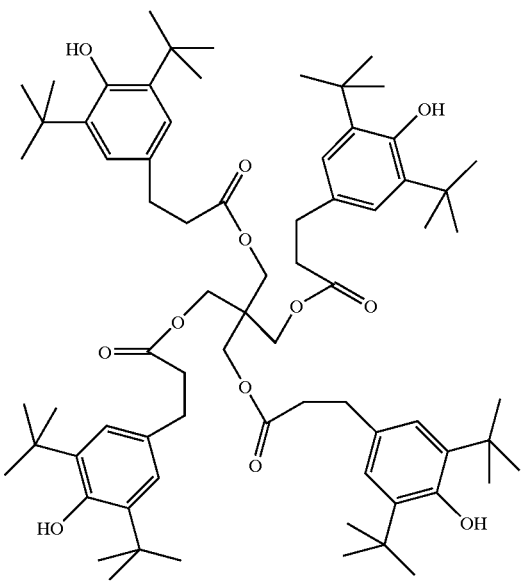
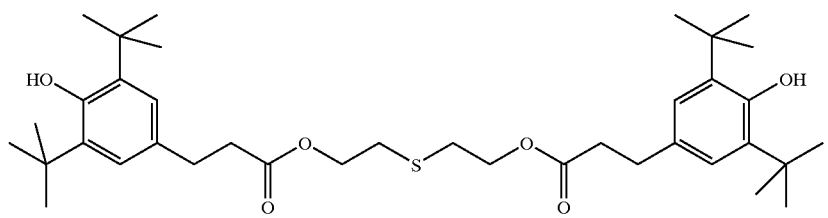
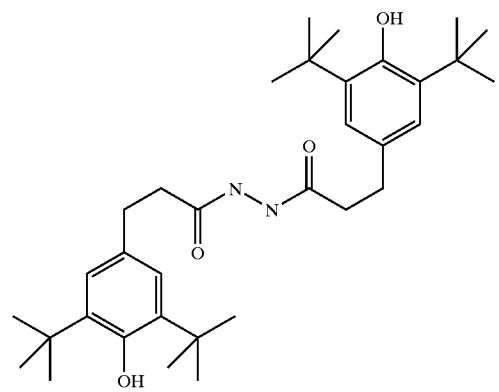

TABLE D-continued
Stabilisers which can be added, for example, to the mixtures according to the invention are indicated below.
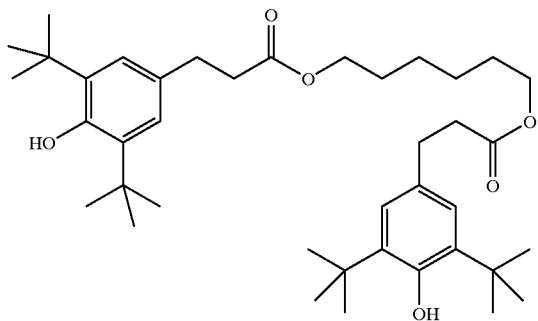
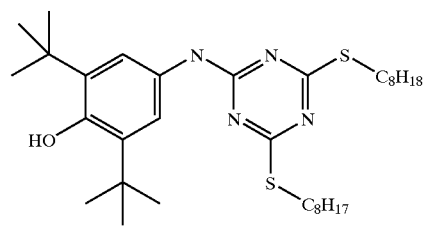
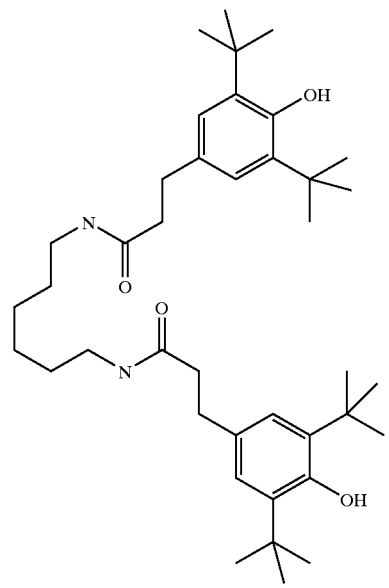

TABLE D-continued
Stabilisers which can be added, for example, to the mixtures according to the invention are indicated below.
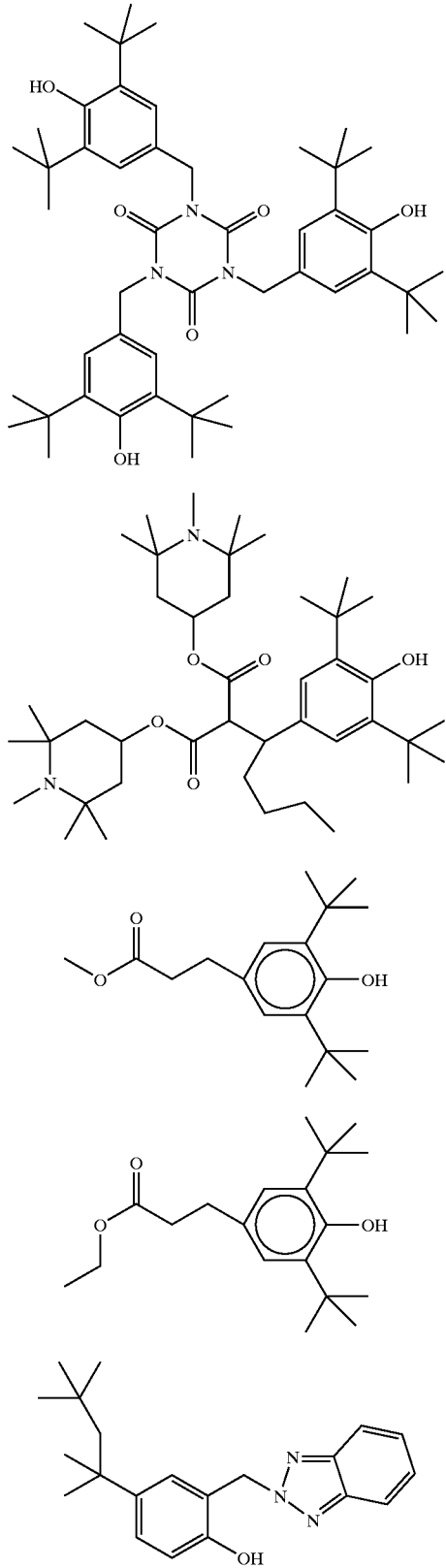

TABLE D-continued
Stabilisers which can be added, for example, to the mixtures according to the invention are indicated below.
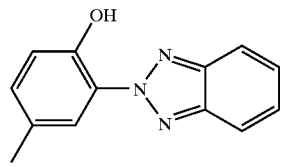
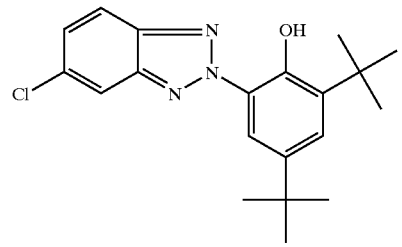
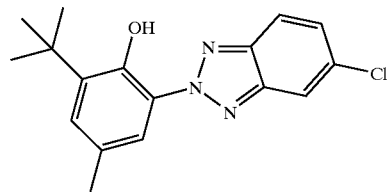
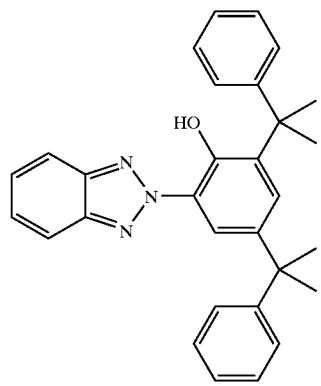
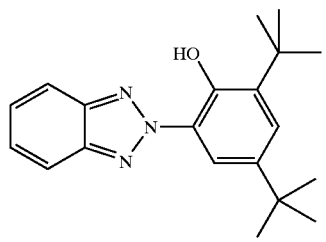
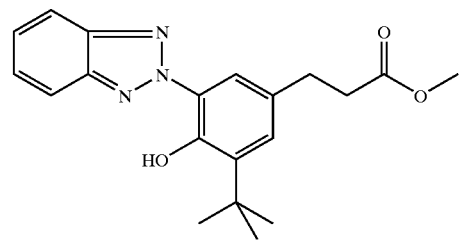

TABLE D-continued
Stabilisers which can be added, for example, to the mixtures according to the invention are indicated below.
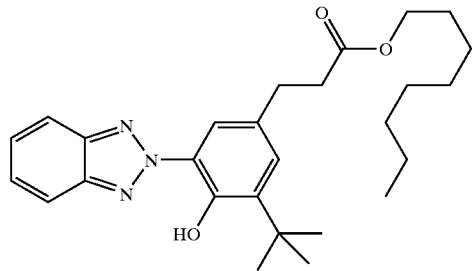
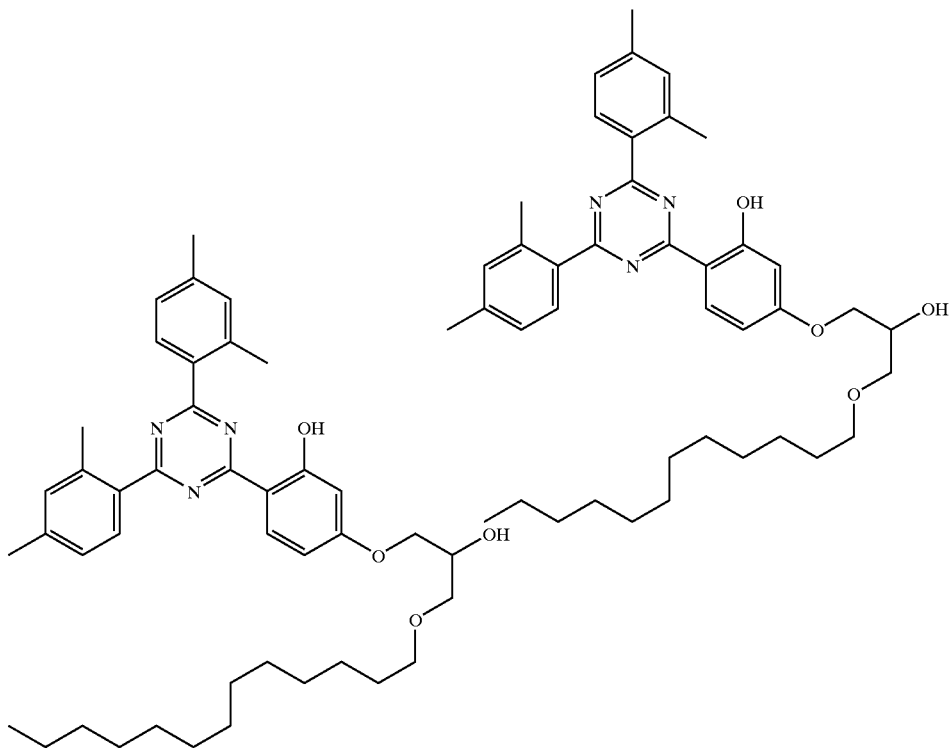
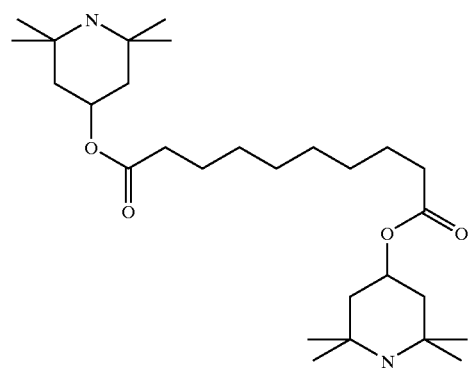

TABLE D-continued

Stabilisers which can be added, for example, to the mixtures according to the invention are indicated below.

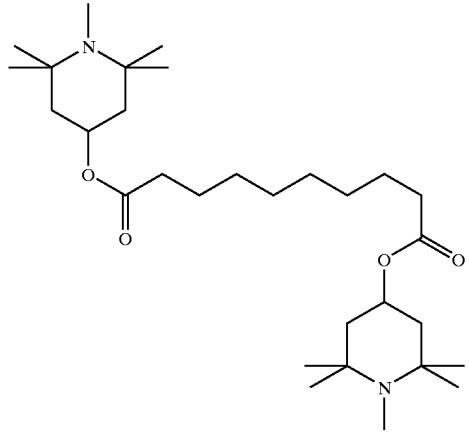

The following examples are intended to explain the invention without restricting it. Above and below, percentages are per cent by weight. All temperatures are given in degrees Celsius. m.p. denotes melting point, cl.p. denotes clearing point. Furthermore, C=crystalline state, N=nematic phase, S=smectic phase and I=isotropic phase. The data between these symbols represent the transition temperatures. Δn denotes optical anisotropy (589 nm, 20° C.), the flow viscosity $v_{20}$ (mm$^2$/sec) was determined at 20° C. The rotational viscosity $\gamma_1$ [mPa·s] was likewise determined at 20° C.

"Conventional work-up" means that water is added if necessary, the mixture is extracted with dichoromethane, diethyl ether, methyl tert-butyl ether or toluene, the phases are separated, the organic phase is dried and evaporated, and the product is purified by distillation under reduced pressure or crystallisation and/or chromatography. The following abbreviations are used:

| | |
|---|---|
| n-BuLi | 1.6 molar solution of n-butyllithium in n-hexane |
| DMAP | 4-(dimethylamino)pyridine |
| THF | tetrahydrofuran |
| DCC | N,N'-dicyclohexylcarbodiimide |

EXAMPLE 1

Step 1.1

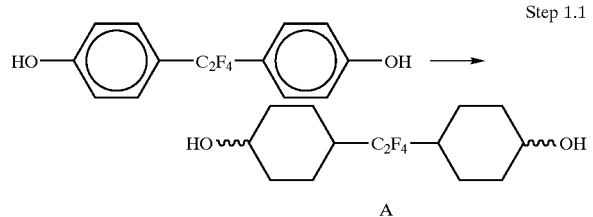

A 3.494 mol of 1,2-bis(4-hydroxyphenyl)tetrafluoroethane are dissolved in 15 l of isopropanol and hydrogenated at 60° C. and 5 bar using 400 g of 5% rhodium/activated carbon. When the hydrogenation is complete, the catalyst is filtered off, the filtrate is evaporated, and the residue is recrystallised from ethyl acetate.

Step 1.2

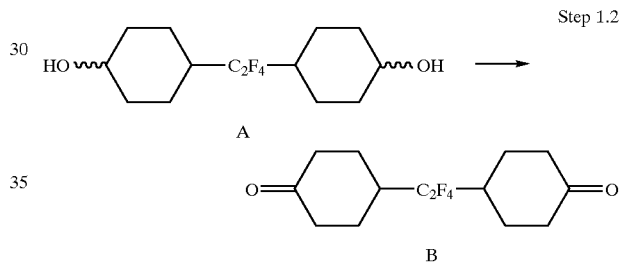

1.5 mol of pyridinium chlorochromate, 300 g of Celite® 545 in 4 l of dichloromethane, and 0.97 mol of A are stirred overnight at room temperature. The suspension is subsequently filtered with suction, the filter cake is washed with dichloromethane, and the filtrate is evaporated. The residue is stirred with 50 ml of petroleum ether/ethyl acetate (1:1), 1 g of activated carbon and 5 g of silica gel and subsequently filtered through silica gel with suction. The filtrate is dissolved in dichloromethane and stirred overnight with 25 g of sulfur trioxide/pyridine complex. Finally, the mixture is extracted with water and filtered through silica gel. m.p.: 125–126° C. (methylcyclohexane)

Step 1.3

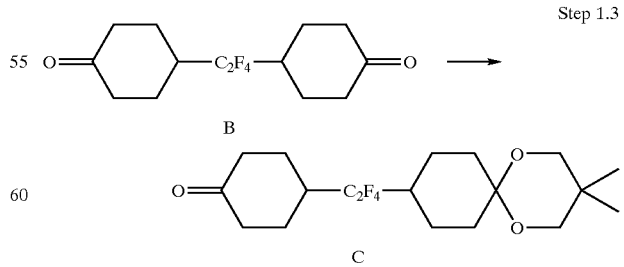

0.075 mol of B and 0.230 mol of 2,2-dimethyl-1,3-propane in 250 ml of cyclohexane are stirred at 60° C. for 24 hours with 0.05 g of sulfuric acid and 250 ml of water.

The mixture is allowed to cool to room temperature, and the sediment is separated off from the liquid phase by means of a frit and dried. Melting range: 146–158° C. (methylcyclohexane)

Step 1.4

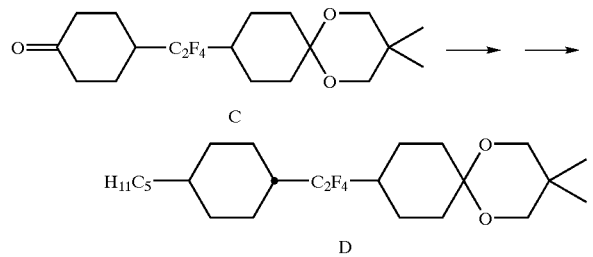

0.121 mol of C and 0.145 mol of pentyltriphenylphosphonium bromide in 400 ml of abs. THF are cooled to –10° C., and 0.160 mol of potassium tert-butoxide in 100 ml of abs. THF is added with stirring. The reaction mixture is stirred overnight at room temperature and subsequently subjected to conventional work up. The crude product is filtered through silica gel with n-hexane. The filtrate is evaporated, the residue is dissolved in 600 ml of THF, 8 g of Pd/C (5%) are added, and the mixture is hydrogenated at room temperature and 1 bar.

Step 1.5

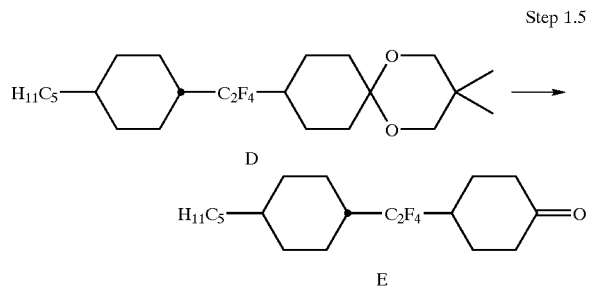

0.041 mol of D, 300 ml of toluene and 100 ml of formic acid are stirred at room temperature for 2 days. The formic acid phase is diluted with water and extracted with toluene, and the combined toluene phases are finally subjected to conventional work-up. Melting range: 64–86.1° C. (methylcyclohexane)

Step 1.6

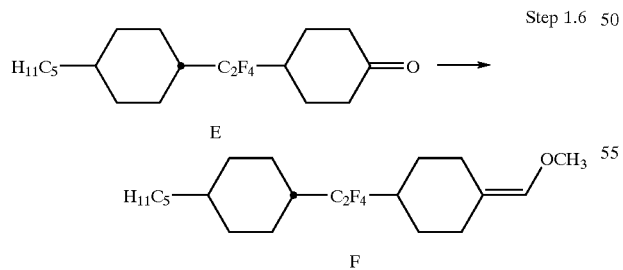

0.105 mol of E and 0.119 mol of methoxymethyltriphenylphosphonium chloride are introduced into 450 ml of THF, and a solution of 0.134 mol of potassium tert-butoxide in 150 ml of THF is added dropwise with ice cooling. The reaction mixture is stirred overnight at room temperature and finally subjected to conventional work-up.

Step 1.7

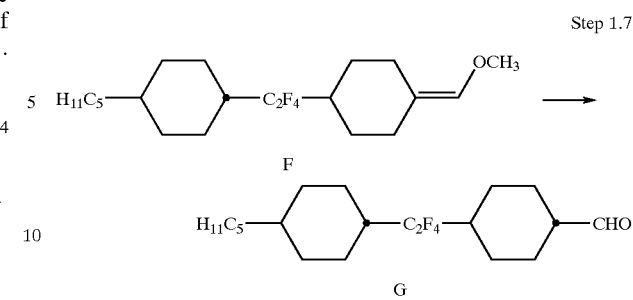

0.061 mol of F and 2.915 mol of formic acid in 200 ml of toluene are stirred overnight at room temperature and subsequently subjected to conventional work-up.

For the isomerisation, 0.083 mol of the product, 600 ml of methanol and 0.135 mol of sodium hydroxide solution are stirred at room temperature for 2 hours. The mixture is subsequently stirred at –20° C. for a further 2 hours. The precipitated product is filtered off with suction and washed with water.

Step 1.8

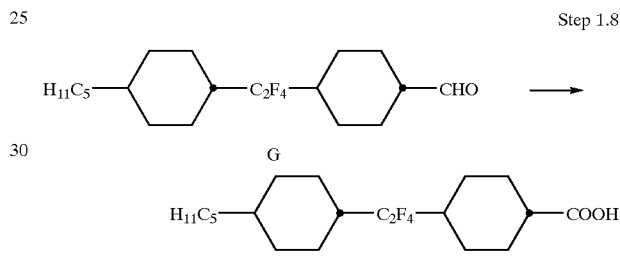

0.107 mol of chromic acid is added at room temperature to 0.042 mol of G in 300 ml of acetone. The mixture is stirred at room temperature for 24 hours. The excess $CrO_3$ is removed using isopropanol. The reaction mixture is finally subjected to conventional work-up. The crude product is recrystallised from acetone at 0° C. C? $S_x$ 253 N 258 I Step 1.9

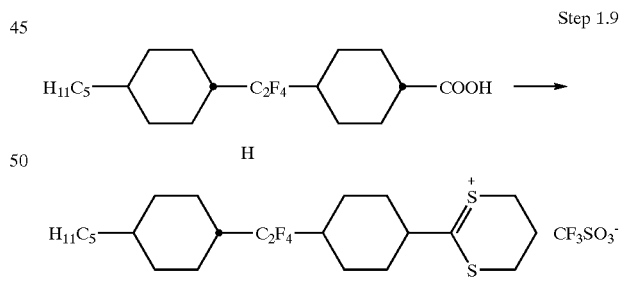

0.018 mol of H is suspended in a mixture of 20 ml of toluene and 20 ml of isooctane, and 0.022 mol of 1,3-propanedithiol is subsequently added to this suspension. The suspension is heated to 60° C., and 0.022 mol of trifluoromethanesulfonic acid is subsequently metered in. The reaction solution is boiled for 3 hours on a water separator. The mixture is allowed to cool to 85° C., and 100 ml of dibutyl ether are added, during which the product crystallises. The crystals are washed with methyl t-butyl ether and dried under reduced pressure. m.p.: 175–182° C.

Step 1.10

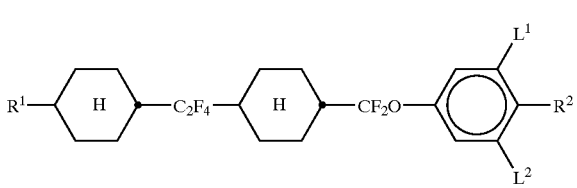

0.012 mol of the triflate I are introduced into 80 ml of dichloromethane, and a mixture of 0.029 mol of triethylamine, 0.015 g of 3,4,5-trifluorophenol dissolved in 50 ml of dichloromethane is added dropwise at −70° C. The reaction mixture is stirred at −70° C. for 1 hour, 0.124 mol of triethylamine trishydrofluoride is added, the mixture is stirred for a further 10 minutes, and 0.063 mol of bromine dissolved in 30 ml of dichloromethane is then added. After the reaction solution has been stirred for 90 minutes, it is allowed to warm to −20° C. and poured into 350 ml of a mixture of 1N NaOH solution and 35 ml of saturated NaHSO$_3$ solution. When the evolution of gas is complete, the organic phase is separated off and subjected to conventional work-up. The product is filtered through silica gel with n-hexane and recrystallised from ethanol. Finally, the product is dissolved in n-heptane and stirred overnight with copper powder. The mixture is evaporated, during which the product crystallises out.

C 36 S$_B$ 123 N 163.9 I; Δ∈=9.1; Δn=0.0815

The following compounds of the formula are prepared analogously:

| R$^1$ | R$^2$ | L$^1$ | L$^2$ | |
|---|---|---|---|---|
| CH$_3$ | F | H | H | |
| CH$_3$ | F | F | H | |
| CH$_3$ | F | F | F | |
| C$_2$H$_5$ | F | H | H | |
| C$_2$H$_5$ | F | F | H | |
| C$_2$H$_5$ | F | F | F | C 33 S$_B$ 100 N 140.5 I |
| n-C$_3$H$_7$ | F | H | H | |
| n-C$_3$H$_7$ | F | F | H | ? −68 S$_B$ 149 N 179.0 I; Δ∈ = 6.2; Δn = 0.0865 |
| n-C$_3$H$_7$ | F | F | F | C 49 S$_B$ 114 N 164.4 I; Δ∈ = 9.9; Δn = 0.0825 |
| C$_4$H$_9$ | F | H | H | |
| C$_4$H$_9$ | F | F | H | |
| C$_4$H$_9$ | F | F | F | |
| C$_5$H$_{11}$ | F | H | H | |
| C$_5$H$_{11}$ | F | F | H | C −15 S$_B$ 157 N 179.3 I; Δ∈ = 6.4; Δn = 0.0835 |
| n-C$_6$H$_{13}$ | F | H | H | |
| n-C$_6$H$_{13}$ | F | F | H | |
| n-C$_6$H$_{13}$ | F | F | F | |
| n-C$_7$H$_{13}$ | F | H | H | |
| n-C$_7$H$_{13}$ | F | F | H | |
| n-C$_7$H$_{13}$ | F | F | F | |
| CH$_2$=CH | F | H | H | |
| CH$_2$=CH | F | F | H | |
| CH$_2$=CH | F | F | F | C 61 S$_?$ (58) N 152.5 I, Δ∈ = 10.0; Δn = 0.0779 |
| CH$_3$CH=CH | F | H | H | |
| CH$_3$CH=CH | F | F | H | |
| CH$_3$CH=CH | F | F | F | |
| CH$_2$=CHC$_2$H$_4$ | F | H | H | |
| CH$_2$=CHC$_2$H$_4$ | F | F | H | |
| CH$_2$=CHC$_2$H$_4$ | F | F | F | |
| CH$_3$CH=CHC$_2$H$_4$ | F | H | H | |
| CH$_3$CH=CHC$_2$H$_4$ | F | F | H | |
| CH$_3$CH=CHC$_2$H$_4$ | F | F | F | |
| (CH$_3$)$_2$CH | F | H | H | |
| (CH$_3$)$_2$CH | F | F | H | |
| (CH$_3$)$_2$CH | F | F | F | |
| (CH$_3$)$_2$CHCH$_2$ | F | H | H | |
| (CH$_3$)$_2$CHCH$_2$ | F | F | H | |
| (CH$_3$)$_2$CHCH$_2$ | F | F | F | |
| CH$_3$ | OCF$_3$ | H | H | |
| CH$_3$ | OCF$_3$ | F | H | |
| CH$_3$ | OCF$_3$ | F | F | |
| C$_2$H$_5$ | OCF$_3$ | H | H | |
| C$_2$H$_5$ | OCF$_3$ | F | H | |
| C$_2$H$_5$ | OCF$_3$ | F | F | |
| n-C$_3$H$_7$ | OCF$_3$ | H | H | |
| n-C$_3$H$_7$ | OCF$_3$ | F | H | C? −48 S$_B$ 160 N 184.4 I; Δ∈ = 8.3; Δn = 0.0866 |
| n-C$_3$H$_7$ | OCF$_3$ | F | F | |
| n-C$_4$H$_9$ | OCF$_3$ | H | H | |
| n-C$_4$H$_9$ | OCF$_3$ | F | H | |
| n-C$_4$H$_9$ | OCF$_3$ | F | F | |
| n-C$_5$H$_{11}$ | OCF$_3$ | H | H | |
| n-C$_5$H$_{11}$ | OCF$_3$ | F | H | |
| n-C$_5$H$_{11}$ | OCF$_3$ | F | F | |
| n-C$_6$H$_{13}$ | OCF$_3$ | H | H | |
| n-C$_6$H$_{13}$ | OCF$_3$ | F | H | |
| n-C$_6$H$_{13}$ | OCF$_3$ | F | F | |
| n-C$_7$H$_{15}$ | OCF$_3$ | H | H | |
| n-C$_7$H$_{15}$ | OCF$_3$ | F | H | |
| n-C$_7$H$_{15}$ | OCF$_3$ | F | F | |
| CH$_2$=CH | OCF$_3$ | H | H | |
| CH$_2$=CH | OCF$_3$ | F | H | |
| CH$_2$=CH | OCF$_3$ | F | F | |
| CH$_3$CH=CH | OCF$_3$ | H | H | |
| CH$_3$CH=CH | OCF$_3$ | F | H | |
| CH$_3$CH=CH | OCF$_3$ | F | F | |
| CH$_2$=CHC$_2$H$_4$ | OCF$_3$ | H | H | |
| CH$_2$=CHC$_2$H$_4$ | OCF$_3$ | F | H | |
| CH$_2$=CHC$_2$H$_4$ | OCF$_3$ | F | F | |
| CH$_3$CH=CHC$_2$H$_4$ | OCF$_3$ | H | H | |
| CH$_3$CH=CHC$_2$H$_4$ | OCF$_3$ | F | H | |
| CH$_3$CH=CHC$_2$H$_4$ | OCF$_3$ | F | F | |
| (CH$_3$)$_2$CH | OCF$_3$ | H | H | |
| (CH$_3$)$_2$CH | OCF$_3$ | F | H | |
| (CH$_3$)$_2$CH | OCF$_3$ | F | F | |
| (CH$_3$)$_2$CHCH$_2$ | OCF$_3$ | H | H | |
| (CH$_3$)$_2$CHCH$_2$ | OCF$_3$ | F | H | |
| (CH$_3$)$_2$CHCH$_2$ | OCF$_3$ | F | F | |
| CH$_3$ | OCHFCF$_3$ | H | H | |
| CH$_3$ | OCHFCF$_3$ | F | H | |
| CH$_3$ | OCHFCF$_3$ | F | F | |
| C$_2$H$_5$ | OCHFCF$_3$ | H | H | |
| C$_2$H$_5$ | OCHFCF$_3$ | F | H | |
| C$_2$H$_5$ | OCHFCF$_3$ | F | F | |
| n-C$_3$H$_7$ | OCHFCF$_3$ | H | H | |
| n-C$_3$H$_7$ | OCHFCF$_3$ | F | H | |
| n-C$_3$H$_7$ | OCHFCF$_3$ | F | F | |

| R¹ | R² | L¹ | L² |
|---|---|---|---|
| n-C₄H₉ | OCHFCF₃ | H | H |
| n-C₄H₉ | OCHFCF₃ | F | H |
| n-C₄H₉ | OCHFCF₃ | F | F |
| n-C₅H₁₁ | OCHFCF₃ | H | H |
| n-C₅H₁₁ | OCHFCF₃ | F | H |
| n-C₅H₁₁ | OCHFCF₃ | F | F |
| n-C₆H₁₃ | OCHFCF₃ | H | H |
| n-C₆H₁₃ | OCHFCF₃ | F | H |
| n-C₆H₁₃ | OCHFCF₃ | F | F |
| CH₂=CH | OCHFCF₃ | H | H |
| CH₂=CH | OCHFCF₃ | F | H |
| CH₂=CH | OCHFCF₃ | F | F |
| CH₃CH=CH | OCHFCF₃ | H | H |
| CH₃CH=CH | OCHFCF₃ | F | H |
| CH₃CH=CH | OCHFCF₃ | F | F |
| CH₂=CHC₂H₄ | OCHFCF₃ | H | H |
| CH₂=CHC₂H₄ | OCHFCF₃ | F | H |
| CH₂=CHC₂H₄ | OCHFCF₃ | F | F |
| CH₃CH=CHC₂H₄ | OCHFCF₃ | H | H |
| CH₃CH=CHC₂H₄ | OCHFCF₃ | F | H |
| CH₃CH=CHC₂H₄ | OCHFCF₃ | F | F |
| (CH₃)₂CH | OCHFCF₃ | H | H |
| (CH₃)₂CH | OCHFCF₃ | F | H |
| (CH₃)₂CH | OCHFCF₃ | F | F |
| (CH₃)₂CHCH₂ | OCHFCF₃ | H | H |
| (CH₃)₂CHCH₂ | OCHFCF₃ | F | H |
| (CH₃)₂CHCH₂ | OCHFCF₃ | F | F |
| CH₃ | OCF₂CHFCF₃ | H | H |
| CH₃ | OCF₂CHFCF₃ | F | H |
| CH₃ | OCF₂CHFCF₃ | F | F |
| C₂H₅ | OCF₂CHFCF₃ | H | H |
| C₂H₅ | OCF₂CHFCF₃ | F | H |
| C₂H₅ | OCF₂CHFCF₃ | F | F |
| n-C₃H₇ | OCF₂CHFCF₃ | H | H |
| n-C₃H₇ | OCF₂CHFCF₃ | F | H |
| n-C₃H₇ | OCF₂CHFCF₃ | F | F |
| n-C₄H₉ | OCF₂CHFCF₃ | H | H |
| n-C₄H₉ | OCF₂CHFCF₃ | F | H |
| n-C₄H₉ | OCF₂CHFCF₃ | F | F |
| n-C₅H₁₁ | OCF₂CHFCF₃ | H | H |
| n-C₅H₁₁ | OCF₂CHFCF₃ | F | H |
| n-C₅H₁₁ | OCF₂CHFCF₃ | F | F |
| n-C₆H₁₃ | OCF₂CHFCF₃ | H | H |
| n-C₆H₁₃ | OCF₂CHFCF₃ | F | H |
| n-C₆H₁₃ | OCF₂CHFCF₃ | F | F |
| CH₂=CH | OCF₂CHFCF₃ | H | H |
| CH₂=CH | OCF₂CHFCF₃ | F | H |
| CH₂=CH | OCF₂CHFCF₃ | F | F |
| CH₃CH=CH | OCF₂CHFCF₃ | H | H |
| CH₃CH=CH | OCF₂CHFCF₃ | F | H |
| CH₃CH=CH | OCF₂CHFCF₃ | F | F |
| CH₂=CHC₂H₄ | OCF₂CHFCF₃ | H | H |
| CH₂=CHC₂H₄ | OCF₂CHFCF₃ | F | H |
| CH₂=CHC₂H₄ | OCF₂CHFCF₃ | F | F |
| CH₃CH=CHC₂H₄ | OCF₂CHFCF₃ | H | H |
| CH₃CH=CHC₂H₄ | OCF₂CHFCF₃ | F | H |
| CH₃CH=CHC₂H₄ | OCF₂CHFCF₃ | F | F |
| (CH₃)₂CH | OCF₂CHFCF₃ | H | H |
| (CH₃)₂CH | OCF₂CHFCF₃ | F | H |
| (CH₃)₂CH | OCF₂CHFCF₃ | F | F |
| (CH₃)₂CHCH₂ | OCF₂CHFCF₃ | H | H |
| (CH₃)₂CHCH₂ | OCF₂CHFCF₃ | F | H |
| (CH₃)₂CHCH₂ | OCF₂CHFCF₃ | F | F |
| CH₃ | OCHF₂ | H | H |
| CH₃ | OCHF₂ | F | H |
| CH₃ | OCHF₂ | F | F |
| C₂H₅ | OCHF₂ | H | H |
| C₂H₅ | OCHF₂ | F | H |
| C₂H₅ | OCHF₂ | F | F |
| n-C₃H₇ | OCHF₂ | H | H |
| n-C₃H₇ | OCHF₂ | F | H |
| n-C₃H₇ | OCHF₂ | F | F |
| n-C₄H₉ | OCHF₂ | H | H |
| n-C₄H₉ | OCHF₂ | F | H |
| n-C₄H₉ | OCHF₂ | F | F |
| n-C₅H₁₁ | OCHF₂ | H | H |
| n-C₅H₁₁ | OCHF₂ | F | H |
| n-C₅H₁₁ | OCHF₂ | F | F |
| n-C₆H₁₃ | OCHF₂ | H | H |
| n-C₆H₁₃ | OCHF₂ | F | H |
| n-C₆H₁₃ | OCHF₂ | F | F |
| CH₂=CH | OCHF₂ | H | H |
| CH₂=CH | OCHF₂ | F | H |
| CH₂=CH | OCHF₂ | F | F |
| CH₃CH=CH | OCHF₂ | H | H |
| CH₃CH=CH | OCHF₂ | F | H |
| CH₃CH=CH | OCHF₂ | F | F |
| CH₂=CHC₂H₄ | OCHF₂ | H | H |
| CH₂=CHC₂H₄ | OCHF₂ | F | H |
| CH₂=CHC₂H₄ | OCHF₂ | F | F |
| CH₃CH=CHC₂H₄ | OCHF₂ | H | H |
| CH₃CH=CHC₂H₄ | OCHF₂ | F | H |
| CH₃CH=CHC₂H₄ | OCHF₂ | F | F |
| (CH₃)₂CH | OCHF₂ | H | H |
| (CH₃)₂CH | OCHF₂ | F | H |
| (CH₃)₂CH | OCHF₂ | F | F |
| (CH₃)₂CHCH₂ | OCHF₂ | H | H |
| (CH₃)₂CHCH₂ | OCHF₂ | F | H |
| (CH₃)₂CHCH₂ | OCHF₂ | F | F |
| CH₃ | CF₃ | H | H |
| CH₃ | CF₃ | F | H |
| CH₃ | CF₃ | F | F |
| C₂H₅ | CF₃ | H | H |
| C₂H₅ | CF₃ | F | H |
| C₂H₅ | CF₃ | F | F |
| n-C₃H₇ | CF₃ | H | H |
| n-C₃H₇ | CF₃ | F | H |
| n-C₃H₇ | CF₃ | F | F |
| n-C₄H₉ | CF₃ | H | H |
| n-C₄H₉ | CF₃ | F | H |
| n-C₄H₉ | CF₃ | F | F |
| n-C₅H₁₁ | CF₃ | H | H |
| n-C₅H₁₁ | CF₃ | F | H |
| n-C₅H₁₁ | CF₃ | F | F |
| n-C₆H₁₃ | CF₃ | H | H |
| n-C₆H₁₃ | CF₃ | F | H |
| n-C₆H₁₃ | CF₃ | F | F |
| CH₂=CH | CF₃ | H | H |
| CH₂=CH | CF₃ | F | H |
| CH₂=CH | CF₃ | F | F |
| CH₃CH=CH | CF₃ | H | H |
| CH₃CH=CH | CF₃ | F | H |
| CH₃CH=CH | CF₃ | F | F |
| CH₂=CHC₂H₄ | CF₃ | H | H |
| CH₂=CHC₂H₄ | CF₃ | F | H |
| CH₂=CHC₂H₄ | CF₃ | F | F |
| CH₃CH=CHC₂H₄ | CF₃ | H | H |
| CH₃CH=CHC₂H₄ | CF₃ | F | H |
| CH₃CH=CHC₂H₄ | CF₃ | F | F |
| (CH₃)₂CH | CF₃ | H | H |
| (CH₃)₂CH | CF₃ | F | H |
| (CH₃)₂CH | CF₃ | F | F |
| (CH₃)₂CHCH₂ | CF₃ | H | H |
| (CH₃)₂CHCH₂ | CF₃ | F | H |
| (CH₃)₂CHCH₂ | CF₃ | F | F |
| CH₃ | CN | H | H |
| CH₃ | CN | F | H |
| CH₃ | CN | F | F |
| C₂H₅ | CN | H | H |
| C₂H₅ | CN | F | H |
| C₂H₅ | CN | F | F |
| n-C₃H₇ | CN | H | H |
| n-C₃H₇ | CN | F | H |
| n-C₃H₇ | CN | F | F |
| n-C₄H₉ | CN | H | H |
| n-C₄H₉ | CN | F | H |
| n-C₄H₉ | CN | F | F |
| n-C₅H₁₁ | CN | H | H |
| n-C₅H₁₁ | CN | F | H |
| n-C₅H₁₁ | CN | F | F |
| n-C₆H₁₃ | CN | H | H |
| n-C₆H₁₃ | CN | F | H |
| n-C₆H₁₃ | CN | F | F |
| CH₂=CH | CN | H | H |

-continued

| R¹ | R² | L¹ | L² |
|---|---|---|---|
| CH$_2$=CH | CN | F | H |
| CH$_2$=CH | CN | F | F |
| CH$_3$CH=CH | CN | H | H |
| CH$_3$CH=CH | CN | F | H |
| CH$_3$CH=CH | CN | F | F |
| CH$_2$=CHC$_2$H$_4$ | CN | H | H |
| CH$_2$=CHC$_2$H$_4$ | CN | F | H |
| CH$_2$=CHC$_2$H$_4$ | CN | F | F |
| CH$_3$CH=CHC$_2$H$_4$ | CN | H | H |
| CH$_3$CH=CHC$_2$H$_4$ | CN | F | H |
| CH$_3$CH=CHC$_2$H$_4$ | CN | F | F |
| (CH$_3$)$_2$CH | CN | H | H |
| (CH$_3$)$_2$CH | CN | F | H |
| (CH$_3$)$_2$CH | CN | F | F |
| (CH$_3$)$_2$CHCH$_2$ | CN | H | H |
| (CH$_3$)$_2$CHCH$_2$ | CN | F | H |
| (CH$_3$)$_2$CHCH$_2$ | CN | F | F |
| CH$_3$ | SF$_5$ | H | H |
| CH$_3$ | SF$_5$ | F | H |
| CH$_3$ | SF$_5$ | F | F |
| C$_2$H$_5$ | SF$_5$ | H | H |
| C$_2$H$_5$ | SF$_5$ | F | H |
| C$_2$H$_5$ | SF$_5$ | F | F |
| n-C$_3$H$_7$ | SF$_5$ | H | H |
| n-C$_3$H$_7$ | SF$_5$ | F | H |
| n-C$_3$H$_7$ | SF$_5$ | F | F |
| n-C$_4$H$_9$ | SF$_5$ | H | H |
| n-C$_4$H$_9$ | SF$_5$ | F | H |
| n-C$_4$H$_9$ | SF$_5$ | F | F |
| n-C$_5$H$_{11}$ | SF$_5$ | H | H |
| n-C$_5$H$_{11}$ | SF$_5$ | F | H |
| n-C$_5$H$_{11}$ | SF$_5$ | F | F |
| n-C$_6$H$_{13}$ | SF$_5$ | H | H |
| n-C$_6$H$_{13}$ | SF$_5$ | F | H |
| n-C$_6$H$_{13}$ | SF$_5$ | F | F |
| CH$_2$=CH | SF$_5$ | H | H |
| CH$_2$=CH | SF$_5$ | F | H |
| CH$_2$=CH | SF$_5$ | F | F |
| CH$_3$CH=CH | SF$_5$ | H | H |
| CH$_3$CH=CH | SF$_5$ | F | H |
| CH$_3$CH=CH | SF$_5$ | F | F |
| CH$_2$=CHC$_2$H$_4$ | SF$_5$ | H | H |
| CH$_2$=CHC$_2$H$_4$ | SF$_5$ | F | H |
| CH$_2$=CHC$_2$H$_4$ | SF$_5$ | F | F |
| CH$_3$CH=CHC$_2$H$_4$ | SF$_5$ | H | H |
| CH$_3$CH=CHC$_2$H$_4$ | SF$_5$ | F | H |
| CH$_3$CH=CHC$_2$H$_4$ | SF$_5$ | F | F |
| (CH$_3$)$_2$CH | SF$_5$ | H | H |
| (CH$_3$)$_2$CH | SF$_5$ | F | H |
| (CH$_3$)$_2$CH | SF$_5$ | F | F |
| (CH$_3$)$_2$CHCH$_2$ | SF$_5$ | H | H |
| (CH$_3$)$_2$CHCH$_2$ | SF$_5$ | F | H |
| (CH$_3$)$_2$CHCH$_2$ | SF$_5$ | F | F |
| CH$_3$ | OCH=CF$_2$ | H | H |
| CH$_3$ | OCH=CF$_2$ | F | H |
| CH$_3$ | OCH=CF$_2$ | F | F |
| C$_2$H$_5$ | OCH=CF$_2$ | H | H |
| C$_2$H$_5$ | OCH=CF$_2$ | F | H |
| C$_2$H$_5$ | OCH=CF$_2$ | F | F |
| n-C$_3$H$_7$ | OCH=CF$_2$ | H | H |
| n-C$_3$H$_7$ | OCH=CF$_2$ | F | H |
| n-C$_3$H$_7$ | OCH=CF$_2$ | F | F |
| n-C$_4$H$_9$ | OCH=CF$_2$ | H | H |
| n-C$_4$H$_9$ | OCH=CF$_2$ | F | H |
| n-C$_4$H$_9$ | OCH=CF$_2$ | F | F |
| n-C$_5$H$_{11}$ | OCH=CF$_2$ | H | H |
| n-C$_5$H$_{11}$ | OCH=CF$_2$ | F | H |
| n-C$_5$H$_{11}$ | OCH=CF$_2$ | F | F |
| n-C$_6$H$_{13}$ | OCH=CF$_2$ | H | H |
| n-C$_6$H$_{13}$ | OCH=CF$_2$ | F | H |
| n-C$_6$H$_{13}$ | OCH=CF$_2$ | F | F |
| CH$_2$=CH | OCH=CF$_2$ | H | H |
| CH$_2$=CH | OCH=CF$_2$ | F | H |
| CH$_2$=CH | OCH=CF$_2$ | F | F |
| CH$_3$CH=CH | OCH=CF$_2$ | H | H |
| CH$_3$CH=CH | OCH=CF$_2$ | F | H |
| CH$_3$CH=CH | OCH=CF$_2$ | F | F |
| CH$_2$=CHC$_2$H$_4$ | OCH=CF$_2$ | H | H |
| CH$_2$=CHC$_2$H$_4$ | OCH=CF$_2$ | F | H |
| CH$_2$=CHC$_2$H$_4$ | OCH=CF$_2$ | F | F |
| CH$_3$CH=CHC$_2$H$_4$ | OCH=CF$_2$ | H | H |
| CH$_3$CH=CHC$_2$H$_4$ | OCH=CF$_2$ | F | H |
| CH$_3$CH=CHC$_2$H$_4$ | OCH=CF$_2$ | F | F |
| (CH$_3$)$_2$CH | OCH=CF$_2$ | H | H |
| (CH$_3$)$_2$CH | OCH=CF$_2$ | F | H |
| (CH$_3$)$_2$CH | OCH=CF$_2$ | F | F |
| (CH$_3$)$_2$CHCH$_2$ | OCH=CF$_2$ | H | H |
| (CH$_3$)$_2$CHCH$_2$ | OCH=CF$_2$ | F | H |
| (CH$_3$)$_2$CHCH$_2$ | OCH=CF$_2$ | F | F |
| CH$_3$ | CH=CF$_2$ | H | H |
| CH$_3$ | CH=CF$_2$ | F | H |
| CH$_3$ | CH=CF$_2$ | F | F |
| C$_2$H$_5$ | CH=CF$_2$ | H | H |
| C$_2$H$_5$ | CH=CF$_2$ | F | H |
| C$_2$H$_5$ | CH=CF$_2$ | F | F |
| n-C$_3$H$_7$ | CH=CF$_2$ | H | H |
| n-C$_3$H$_7$ | CH=CF$_2$ | F | H |
| n-C$_3$H$_7$ | CH=CF$_2$ | F | F |
| n-C$_4$H$_9$ | CH=CF$_2$ | H | H |
| n-C$_4$H$_9$ | CH=CF$_2$ | F | H |
| n-C$_4$H$_9$ | CH=CF$_2$ | F | F |
| n-C$_5$H$_{11}$ | CH=CF$_2$ | H | H |
| n-C$_5$H$_{11}$ | CH=CF$_2$ | F | H |
| n-C$_5$H$_{11}$ | CH=CF$_2$ | F | F |
| n-C$_6$H$_{13}$ | CH=CF$_2$ | H | H |
| n-C$_6$H$_{13}$ | CH=CF$_2$ | F | H |
| n-C$_6$H$_{13}$ | CH=CF$_2$ | F | F |
| CH$_2$=CH | CH=CF$_2$ | H | H |
| CH$_2$=CH | CH=CF$_2$ | F | H |
| CH$_2$=CH | CH=CF$_2$ | F | F |
| CH$_3$CH=CH | CH=CF$_2$ | H | H |
| CH$_3$CH=CH | CH=CF$_2$ | F | H |
| CH$_3$CH=CH | CH=CF$_2$ | F | F |
| CH$_2$=CHC$_2$H$_4$ | CH=CF$_2$ | H | H |
| CH$_2$=CHC$_2$H$_4$ | CH=CF$_2$ | F | H |
| CH$_2$=CHC$_2$H$_4$ | CH=CF$_2$ | F | F |
| CH$_3$CH=CHC$_2$H$_4$ | CH=CF$_2$ | H | H |
| CH$_3$CH=CHC$_2$H$_4$ | CH=CF$_2$ | F | H |
| CH$_3$CH=CHC$_2$H$_4$ | CH=CF$_2$ | F | F |
| (CH$_3$)$_2$CH | CH=CF$_2$ | H | H |
| (CH$_3$)$_2$CH | CH=CF$_2$ | F | H |
| (CH$_3$)$_2$CH | CH=CF$_2$ | F | F |
| (CH$_3$)$_2$CHCH$_2$ | CH=CF$_2$ | H | H |
| (CH$_3$)$_2$CHCH$_2$ | CH=CF$_2$ | F | H |
| (CH$_3$)$_2$CHCH$_2$ | CH=CF$_2$ | F | F |
| CH$_3$ | CF=CF$_2$ | H | H |
| CH$_3$ | CF=CF$_2$ | F | H |
| CH$_3$ | CF=CF$_2$ | F | F |
| C$_2$H$_5$ | CF=CF$_2$ | H | H |
| C$_2$H$_5$ | CF=CF$_2$ | F | H |
| C$_2$H$_5$ | CF=CF$_2$ | F | F |
| n-C$_3$H$_7$ | CF=CF$_2$ | H | H |
| n-C$_3$H$_7$ | CF=CF$_2$ | F | H |
| n-C$_3$H$_7$ | CF=CF$_2$ | F | F |
| n-C$_4$H$_9$ | CF=CF$_2$ | H | H |
| n-C$_4$H$_9$ | CF=CF$_2$ | F | H |
| n-C$_4$H$_9$ | CF=CF$_2$ | F | F |
| n-C$_5$H$_{11}$ | CF=CF$_2$ | H | H |
| n-C$_5$H$_{11}$ | CF=CF$_2$ | F | H |
| n-C$_5$H$_{11}$ | CF=CF$_2$ | F | F |
| n-C$_6$H$_{13}$ | CF=CF$_2$ | H | H |
| n-C$_6$H$_{13}$ | CF=CF$_2$ | F | H |
| n-C$_6$H$_{13}$ | CF=CF$_2$ | F | F |
| CH$_2$=CH | CF=CF$_2$ | H | H |
| CH$_2$=CH | CF=CF$_2$ | F | H |
| CH$_2$=CH | CF=CF$_2$ | F | F |
| CH$_3$CH=CH | CF=CF$_2$ | H | H |
| CH$_3$CH=CH | CF=CF$_2$ | F | H |
| CH$_3$CH=CH | CF=CF$_2$ | F | F |
| CH$_2$=CHC$_2$H$_4$ | CF=CF$_2$ | H | H |
| CH$_2$=CHC$_2$H$_4$ | CF=CF$_2$ | F | H |
| CH$_2$=CHC$_2$H$_4$ | CF=CF$_2$ | F | F |
| CH$_3$CH=CHC$_2$H$_4$ | CF=CF$_2$ | H | H |
| CH$_3$CH=CHC$_2$H$_4$ | CF=CF$_2$ | F | H |
| CH$_3$CH=CHC$_2$H$_4$ | CF=CF$_2$ | F | F |

-continued

| R¹ | R² | L¹ | L² |
|---|---|---|---|
| $(CH_3)_2CH$ | $CF=CF_2$ | H | H |
| $(CH_3)_2CH$ | $CF=CF_2$ | F | H |
| $(CH_3)_2CH$ | $CF=CF_2$ | F | F |
| $(CH_3)_2CHCH_2$ | $CF=CF_2$ | H | H |
| $(CH_3)_2CHCH_2$ | $CF=CF_2$ | F | H |
| $(CH_3)_2CHCH_2$ | $CF=CF_2$ | F | F |
| $CH_3$ | $OCF=CF_2$ | H | H |
| $CH_3$ | $OCF=CF_2$ | F | H |
| $CH_3$ | $OCF=CF_2$ | F | F |
| $C_2H_5$ | $OCF=CF_2$ | H | H |
| $C_2H_5$ | $OCF=CF_2$ | F | H |
| $C_2H_5$ | $OCF=CF_2$ | F | F |
| $n-C_3H_7$ | $OCF=CF_2$ | H | H |
| $n-C_3H_7$ | $OCF=CF_2$ | F | H |
| $n-C_3H_7$ | $OCF=CF_2$ | F | F |
| $n-C_4H_9$ | $OCF=CF_2$ | H | H |
| $n-C_4H_9$ | $OCF=CF_2$ | F | H |
| $n-C_4H_9$ | $OCF=CF_2$ | F | F |
| $n-C_5H_{11}$ | $OCF=CF_2$ | H | H |
| $n-C_5H_{11}$ | $OCF=CF_2$ | F | H |
| $n-C_5H_{11}$ | $OCF=CF_2$ | F | F |
| $n-C_6H_{13}$ | $OCF=CF_2$ | H | H |
| $n-C_6H_{13}$ | $OCF=CF_2$ | F | H |
| $n-C_6H_{13}$ | $OCF=CF_2$ | F | F |
| $CH_2=CH$ | $OCF=CF_2$ | H | H |
| $CH_2=CH$ | $OCF=CF_2$ | F | H |
| $CH_2=CH$ | $OCF=CF_2$ | F | F |
| $CH_3CH=CH$ | $OCF=CF_2$ | H | H |
| $CH_3CH=CH$ | $OCF=CF_2$ | F | H |
| $CH_3CH=CH$ | $OCF=CF_2$ | F | F |
| $CH_2=CHC_2H_4$ | $OCF=CF_2$ | H | H |
| $CH_2=CHC_2H_4$ | $OCF=CF_2$ | F | H |
| $CH_2=CHC_2H_4$ | $OCF=CF_2$ | F | F |
| $CH_3CH=CHC_2H_4$ | $OCF=CF_2$ | H | H |
| $CH_3CH=CHC_2H_4$ | $OCF=CF_2$ | F | H |
| $CH_3CH=CHC_2H_4$ | $OCF=CF_2$ | F | F |
| $(CH_3)_2CH$ | $OCF=CF_2$ | H | H |
| $(CH_3)_2CH$ | $OCF=CF_2$ | F | H |
| $(CH_3)_2CH$ | $OCF=CF_2$ | F | F |
| $(CH_3)_2CHCH_2$ | $OCF=CF_2$ | H | H |
| $(CH_3)_2CHCH_2$ | $OCF=CF_2$ | F | H |
| $(CH_3)_2CHCH_2$ | $OCF=CF_2$ | F | F |

EXAMPLE 2

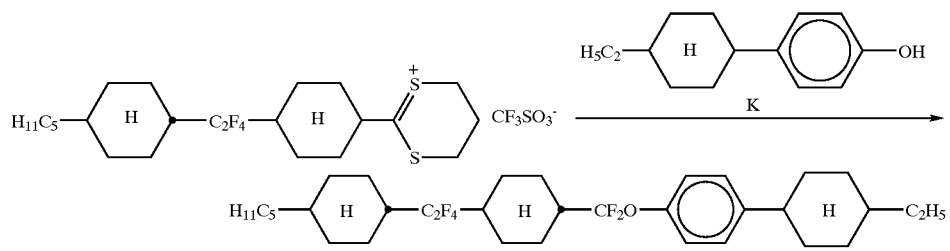

0.014 mol of the triflate I (from step 1.9) is introduced into 80 ml of dichloromethane at −70° C., and a mixture of 0.032 mol of triethylamine and 0.028 mol of K in 50 ml of dichloromethane is added dropwise. The mixture is stirred at −70° C. for 1 hour, 0.140 mol of triethylamine trishydrofluoride is added, the mixture is stirred for a further 10 minutes, and 0.070 mol of 1,3-dibromo-5,5-dimethylhydantoin suspended in 50 ml of dichloromethane is added. After the reaction solution has been stirred for 90 minutes, it is allowed to warm to 20° C., and the solution is poured into a mixture consisting of 1N NaOH solution and 35 ml of saturated $NaHSO_3$ solution. When the evolution of gas is complete, the organic phase is separated off, and the aqueous phase is extracted with dichloromethane. The combined organic phases are finally subjected to conventional work-up.

C 97 $S_B$ 219 N 277.9 I; $\Delta\epsilon=1.9$; $\Delta n=0.1055$

The following compounds of the formula

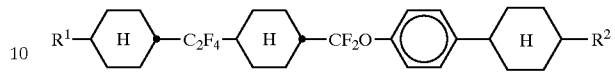

are prepared analogously.

| R¹ | R² |
|---|---|
| $CH_3$ | $CH_3$ |
| $CH_3$ | $C_2H_5$ |
| $CH_3$ | $n-C_3H_7$ |
| $CH_3$ | $n-C_4H_9$ |
| $CH_3$ | $n-C_5H_{11}$ |
| $CH_3$ | $n-C_6H_{13}$ |
| $C_2H_5$ | $CH_3$ |
| $C_2H_5$ | $C_2H_5$ |
| $C_2H_5$ | $n-C_3H_7$ |
| $C_2H_5$ | $n-C_4H_9$ |
| $C_2H_5$ | $n-C_5H_{11}$ |
| $C_2H_5$ | $n-C_6H_{13}$ |
| $n-C_3H_7$ | $CH_3$ |
| $n-C_3H_7$ | $C_2H_5$ |
| $n-C_3H_7$ | $n-C_3H_7$ |
| $n-C_3H_7$ | $n-C_4H_9$ |
| $n-C_3H_7$ | $n-C_5H_{11}$ |
| $n-C_3H_7$ | $n-C_6H_{13}$ |
| $n-C_4H_9$ | $CH_3$ |
| $n-C_4H_9$ | $C_2H_5$ |
| $n-C_4H_9$ | $n-C_3H_7$ |
| $n-C_4H_9$ | $n-C_4H_9$ |
| $n-C_4H_9$ | $n-C_5H_{11}$ |
| $n-C_4H_9$ | $n-C_6H_{13}$ |
| $n-C_5H_{11}$ | $CH_3$ |
| $n-C_5H_{11}$ | $n-C_3H_7$ |
| $n-C_5H_{11}$ | $n-C_4H_9$ |
| $n-C_5H_{11}$ | $n-C_5H_{11}$ |
| $n-C_5H_{11}$ | $n-C_6H_{13}$ |
| $n-C_6H_{13}$ | $CH_3$ |

-continued

| R¹ | R² |
|---|---|
| $n-C_6H_{13}$ | $C_2H_5$ |
| $n-C_6H_{13}$ | $n-C_3H_7$ |
| $n-C_6H_{13}$ | $n-C_4H_9$ |
| $n-C_6H_{13}$ | $n-C_5H_{11}$ |
| $n-C_6H_{13}$ | $n-C_6H_{13}$ |
| $CH_2=CH$ | $CH_3$ |
| $CH_2=CH$ | $C_2H_5$ |

-continued

| R¹ | R² |
|---|---|
| $CH_2=CH$ | $n\text{-}C_3H_7$ |
| $CH_2=CH$ | $n\text{-}C_4H_9$ |
| $CH_2=CH$ | $n\text{-}C_5H_{11}$ |
| $CH_2=CH$ | $n\text{-}C_6H_{13}$ |
| $CH_3$ | $CH_2=CH$ |
| $C_2H_5$ | $CH_2=CH$ |
| $n\text{-}C_3H_7$ | $CH_2=CH$ |
| $n\text{-}C_4H_9$ | $CH_2=CH$ |
| $n\text{-}C_5H_{11}$ | $CH_2=CH$ |
| $n\text{-}C_6H_{13}$ | $CH_2=CH$ |
| $CH_3CH=CH$ | $CH_3$ |
| $CH_3CH=CH$ | $C_2H_5$ |
| $CH_3CH=CH$ | $n\text{-}C_3H_7$ |
| $CH_3CH=CH$ | $n\text{-}C_4H_9$ |
| $CH_3CH=CH$ | $n\text{-}C_5H_{11}$ |
| $CH_3CH=CH$ | $n\text{-}C_6H_{13}$ |
| $CH_2=CH\text{-}C_2H_4$ | $CH_3$ |
| $CH_2=CH\text{-}C_2H_4$ | $C_2H_5$ |
| $CH_2=CH\text{-}C_2H_4$ | $n\text{-}C_3H_7$ |
| $CH_2=CH\text{-}C_2H_4$ | $n\text{-}C_4H_9$ |
| $CH_2=CH\text{-}C_2H_4$ | $n\text{-}C_5H_{11}$ |
| $CH_2=CH\text{-}C_2H_4$ | $n\text{-}C_6H_{13}$ |
| $(CH_3)_2CH$ | $CH_3$ |
| $(CH_3)_2CH$ | $C_2H_5$ |
| $(CH_3)_2CH$ | $n\text{-}C_3H_7$ |
| $(CH_3)_2CH$ | $n\text{-}C_4H_9$ |
| $(CH_3)_2CH$ | $n\text{-}C_5H_{11}$ |
| $(CH_3)_2CH$ | $n\text{-}C_6H_{13}$ |
| $(CH_3)_2CHCH_2$ | $CH_3$ |
| $(CH_3)_2CHCH_2$ | $C_2H_5$ |
| $(CH_3)_2CHCH_2$ | $n\text{-}C_3H_7$ |
| $(CH_3)_2CHCH_2$ | $n\text{-}C_4H_9$ |
| $(CH_3)_2CHCH_2$ | $n\text{-}C_5H_{11}$ |
| $(CH_3)_2CHCH_2$ | $n\text{-}C_6H_{13}$ |

Mixture Examples

Example M1

| | | | |
|---|---|---|---|
| BCH-3F.F | 10.83% | Clearing point [° C.]: | 96.2 |
| BCH-5F.F | 9.02% | d · Δn [μm]: | 0.50 |
| ECCP-30CF$_3$ | 4.51% | Twist [°]: | 90 |
| ECCP-50CF$_3$ | 4.51% | γ$_1$ [mPa · s, 20° C.]: | 144 |
| CBC-33F | 1.80% | | |
| CBC-53F | 1.80% | | |
| CBC-55F | 1.80% | | |
| PCH-6F | 7.22% | | |
| PCH-7F | 5.41% | | |
| CCP-20CF$_3$ | 7.22% | | |
| CCP-30CF$_3$ | 10.83% | | |
| CCP-40CF$_3$ | 6.32% | | |
| CCP-50CF$_3$ | 9.92% | | |
| PCH-5F | 9.02% | | |
| CWCQU-3-F | 9.78% | | |

Example M2

| | | | |
|---|---|---|---|
| PCH-5F | 3.20% | Clearing point [° C.]: | 132.3 |
| CCP-20CF$_2$.F.F | 17.04% | Δε [kHz, 20° C.]: | 9.2 |
| CCP-30CF$_2$.F.F | 16.00% | d · Δn [μm]: | 0.50 |
| CCP-50CF$_2$.F.F | 17.04% | Twist [°]: | 90 |
| CUP-2F.F | 5.36% | | |
| CUP-3F.F | 5.36% | | |
| CBC-33F | 5.36% | | |
| CBC-53F | 5.36% | | |
| CBC-55F | 5.28% | | |
| CWCQU-3-F | 20.02% | | |

Example M3 (for 4 V drivers)

| | | | |
|---|---|---|---|
| CC-5-V | 2.0% | Clearing point [° C.]: | 102.6 |
| CCG-V-F | 10.0% | Δn [589 nm, 20° C.]: | 0.0825 |
| CCP-20CF$_3$.F | 12.0% | Δε [1 kHz, 20° C.]: | 6.8 |
| CCP-30CF$_3$.F | 12.0% | γ$_1$ [mPa · s, 20° C.]: | 147 |
| CCP-20CF$_3$ | 9.0% | d · Δn [μm]: | 0.50 |
| CCP-30CF$_3$ | 9.0% | Twist [°]: | 90 |
| CCP-40CF$_3$ | 8.0% | | |
| CCP-3F.F.F | 10.0% | | |
| CCP-5F.F.F | 8.0% | | |
| CWCQU-3-F | 10.0% | | |
| CC-3-V1 | 10.0% | | |

Mixture M4 (for 4 V drivers)

| | | | |
|---|---|---|---|
| CC-5-V | 7.0% | Clearing point [° C.]: | 102.5 |
| CCG-V-F | 10.0% | Δn [589 nm, 20° C.]: | 0.0832 |
| CCP-20CF$_3$.F | 12.0% | Δε [1 kHz, 20° C.]: | 6.8 |
| CCP-30CF$_3$.F | 12.0% | γ$_1$ [mPa · s, 20° C.]: | 146 |
| CCP-20CF$_3$ | 9.0% | d · Δn [μm]: | 0.50 |
| CCP-30CF$_3$ | 9.0% | Twist [°]: | 90 |
| CCP-3F.F.F | 10.0% | | |
| CCP-5F.F.F | 7.0% | | |
| CWCQU-3-F | 8.0% | | |
| CCGU-3-F | 6.0% | | |
| CC-3-V1 | 10.0% | | |

Example M5 (for 4 V drivers)

| | | | |
|---|---|---|---|
| CC-5-V | 11.0% | Clearing point [° C.]: | 102.3 |
| CCG-V-F | 10.0% | Δn [589 nm, 20° C.]: | 0.0845 |
| CCP-20CF$_3$.F | 12.0% | Δε [1 kHz, 20° C.]: | 6.8 |
| CCP-30CF$_3$.F | 12.0% | γ$_1$ [mPa · s, 20° C.]: | 145 |
| CCP-20CF$_3$ | 9.0% | d · Δn [μm]: | 0.50 |
| CCP-30CF$_3$ | 9.0% | Twist [°]: | 90 |
| CCP-3F.F.F | 11.0% | | |
| CBC-33F | 4.0% | | |
| CWCQU-n-F | 10.0% | | |
| CCGU-3-F | 6.0% | | |
| PCH-7F | 6.0% | | |

Example M6 (for 3.3 V drivers)

| | | | |
|---|---|---|---|
| CCP-30CF$_3$ | 8.0% | Clearing point [° C.]: | 72.5 |
| CCP-40CF$_3$ | 5.0% | Δn [589 nm, 20° C.]: | 0.0908 |
| CCP-20CF$_3$.F | 12.0% | Δε [1 kHz, 20° C.]: | 9.8 |
| CCP-30CF$_3$.F | 12.0% | γ$_1$ [mPa · s, 20° C.]: | 141 |
| CCP-2F.F.F | 11.0% | d · Δn [μm]: | 0.50 |
| CCP-3F.F.F | 9.0% | Twist [°]: | 90 |
| CGU-2-F | 10.0% | | |
| CGU-3-F | 10.0% | | |
| CGU-5-F | 9.0% | | |
| CWCQU-3-F | 8.5% | | |
| CC-3-V1 | 5.5% | | |

Example M7 (for 3.3 V drivers)

| | | | |
|---|---|---|---|
| CCP-20CF$_3$ | 8.0% | Clearing point [° C.]: | 72.5 |
| CCP-30CF$_3$ | 8.0% | | |
| CCP-40CF$_3$ | 8.0% | Δε [1 kHz, 20° C.]: | 9.9 |

-continued

Example M7 (for 3.3 V drivers)

| | | | | |
|---|---|---|---|---|
| CCP-20CF$_3$.F | 12.0% | $\gamma_1$ [mPa · s, 20° C.]: | 143 | |
| CCP-2F.F.F | 11.0% | d · $\Delta$n [$\mu$m]: | 0.50 | |
| CCP-3F.F.F | 8.5% | Twist [°]: | 90 | |
| CGU-2-F | 10.0% | | | |
| CGU-3-F | 10.0% | | | |
| CGU-5-F | 5.0% | | | |
| CCGU-3-F | 3.5% | | | |
| CCH-3CF$_3$ | 6.0% | | | |
| CWCQU-3-F | 10.0% | | | |

Example M8 (low $\Delta$n)

| | | | |
|---|---|---|---|
| CC-5V | 3.0% | Clearing point [° C.]: | 79.5 |
| CCH-3CF$_3$ | 7.0% | $\Delta$n [589 nm, 20° C.]: | 0.0709 |
| CCH-5CF$_3$ | 8.0% | $\Delta\epsilon$ [1 kHz, 20° C.]: | 9.6 |
| CCP-2F.F.F | 11.0% | $\gamma_1$ [mPa · s, 20° C.]: | 151 |
| CCP-3F.F.F | 12.0% | VHR [%]: | 98.3 |
| CCP-5F.F.F | 5.0% | V$_{10}$ [V]: | 1.42 |
| CCP-20CF$_3$.F | 12.0% | | |
| CCP-30CF$_3$.F | 6.0% | | |
| CGU-2-F | 8.0% | | |
| CCOC-4-3 | 3.0% | | |
| CWCQU-3-F | 25.0% | | |

Example M9 (low $\Delta$n)

| | | | |
|---|---|---|---|
| CCP-2F.F.F | 11.0% | Clearing point [° C.]: | 78.5 |
| CCP-3F.F.F | 12.0% | $\Delta$n [589 nm, 20° C.]: | 0.0654 |
| CCP-5F.F.F | 5.0% | VHR [%]: | 97.5 |
| CCZU-2-F | 5.0% | d · $\Delta$n [$\mu$m]: | 0.50 |
| CCZU-3-F | 16.0% | Twist [° C.]: | 90 |
| CCZU-5-F | 4.0% | V$_{10}$ [V]: | 1.29 |
| CCH-3CF$_3$ | 8.0% | | |
| CCH-5CF$_3$ | 8.0% | | |
| PCH-7F | 5.0% | | |
| CWCQU-n-F | 26.0% | | |

Example M10 (for 3.3 V drivers)

| | | | |
|---|---|---|---|
| CCP-2F.F.F | 7.0% | Clearing point [° C.]: | 83.5 |
| CCP-3F.F.F | 10.0% | $\Delta$n [589 nm, 20° C.]: | 0.0932 |
| CCP-30CF$_3$.F | 12.0% | $\Delta\epsilon$ [1 kHz, 20° C.]: | 10.9 |
| CCP-20CF$_3$ | 7.0% | $\gamma_1$ [mPa · s, 20° C.]: | 184 |
| CCP-30CF$_3$ | 8.0% | | |
| CGU-2-F | 10.0% | | |
| CGU-3-F | 10.0% | | |
| CGU-5-F | 10.5% | | |
| CCG-V-F | 7.5% | | |
| CWCQU-3-F | 8.0% | | |
| CWCQU-5-F | 10.0% | | |

Example M11 (for 3.8 V or 4 V drivers)

| | | | |
|---|---|---|---|
| PGU-2-F | 7.0% | Clearing point [° C.]: | 72.0 |
| PGU-3-F | 2.0% | $\Delta$n [589 nm, 20° C.]: | 0.0936 |
| CGZP-2-OT | 5.0% | $\gamma_1$ [mPa · s, 20° C.]: | 78 |
| CGZP-3-OT | 2.0% | V$_{10, 0, 20}$ [V]: | 1.55 |

Example M11 (for 3.8 V or 4 V drivers)

| | |
|---|---|
| BCH-3F.F | 15.0% |
| CCP-2F.F.F | 10.0% |
| CCZU-2-F | 3.0% |
| CC-3-V1 | 12.0% |
| CC-5-V | 15.0% |
| CCH-35 | 6.0% |
| PCH-302 | 10.0% |
| CCP-V-1 | 4.0% |
| CWCQU-2-F | 4.0% |
| CWCQU-3-F | 5.0% |

Example M12

| | | | |
|---|---|---|---|
| BCH-3F.F | 10.8% | Clearing point [° C.]: | 96.2 |
| BCH-5F.F | 9.0% | $\Delta$n [589 nm, 20° C.]: | 0.0950 |
| ECCP-30CF$_3$ | 4.5% | $\Delta\epsilon$ [1 kHz, 20° C.]: | 5.7 |
| ECCP-50CF$_3$ | 4.5% | | |
| CBC-33F | 1.8% | | |
| CBC-53F | 1.8% | | |
| CBC-55F | 1.8% | | |
| PCH-6F | 7.2% | | |
| PCH-7F | 5.4% | | |
| CCP-20CF$_3$ | 7.2% | | |
| CCP-30CF$_3$ | 10.8% | | |
| CCP-40CF$_3$ | 6.3% | | |
| CCP-50CF$_3$ | 9.9% | | |
| PCH-5F | 9.0% | | |
| CWCQU-5-F | 10.0% | | |

Example M13

| | | | |
|---|---|---|---|
| BCH-3F.F | 10.8% | Clearing point [° C.]: | 93.7 |
| BCH-5F.F | 9.0% | $\gamma_1$ [mPa · s, 20° C.]: | 184 |
| ECCP-30CF$_3$ | 4.5% | | |
| ECCP-50CF$_3$ | 4.5% | | |
| CBC-33F | 1.8% | | |
| CBC-53F | 1.8% | | |
| CBC-55F | 1.8% | | |
| PCH-6F | 7.2% | | |
| PCH-7F | 5.4% | | |
| CCP-20CF$_3$ | 7.2% | | |
| CCP-30CF$_3$ | 10.8% | | |
| CCP-40CF$_3$ | 6.3% | | |
| CCP-50CF$_3$ | 9.9% | | |
| PCH-5F | 9.0% | | |
| CWCQU-2-F | 10.0% | | |

Example M14

| | | | |
|---|---|---|---|
| BCH-3F.F | 10.8% | Clearing point [° C.]: | 94.4 |
| BCH-5F.F | 9.0% | $\Delta$n [589 nm, 20° C.]: | 0.0951 |
| ECCP-30CF$_3$ | 4.5% | $\Delta\epsilon$ [1 kHz, 20° C.]: | 5.7 |
| ECCP-50CF$_3$ | 4.5% | | |
| CBC-33F | 1.8% | | |
| CBC-53F | 1.8% | | |
| CBC-55F | 1.8% | | |
| PCH-6F | 7.2% | | |
| PCH-7F | 5.4% | | |
| CCP-20CF$_3$ | 7.2% | | |
| CCP-30CF$_3$ | 10.8% | | |
| CCP-40CF$_3$ | 6.3% | | |
| CCP-50CF$_3$ | 9.9% | | |
| PCH-5F | 9.0% | | |
| CWCQU-V-F | 10.0% | | |

| Example M15 | | | |
|---|---|---|---|
| BCH-3F.F | 10.8% | Clearing point[° C.]: | 109.9 |
| BCH-5F.F | 9.0% | Δn [589 nm, 20° C.]: | 0.0974 |
| ECCP-30CF$_3$ | 4.5% | Δε [1 kHz, 20° C.]: | 4.9 |
| ECCP-50CF$_3$ | 4.5% | | |
| CBC-33F | 1.8% | | |
| CBC-53F | 1.8% | | |
| CBC-55F | 1.8% | | |
| PCH-6F | 7.2% | | |
| PCH-7F | 5.4% | | |
| CCP-20CF$_3$ | 7.2% | | |
| CCP-30CF$_3$ | 10.8% | | |
| CCP-40CF$_3$ | 6.3% | | |
| CCP-50CF$_3$ | 9.9% | | |
| PCH-5F | 9.0% | | |
| CWCQPC-5-2 | 10.0% | | |

| Example M16 | | | |
|---|---|---|---|
| BCH-3F.F | 10.8% | Clearing point[° C.]: | 98.6 |
| BCH-5F.F | 9.05 | Δn [589 nm, 20° C.]: | 0.0952 |
| ECCP-30CF$_3$ | 4.5% | Δε [1 kHz, 20° C.]: | 5.4 |
| ECCP-50CF$_3$ | 4.5% | | |
| CBC-33F | 1.8% | | |
| CBC-53F | 1.8% | | |
| CBC-55F | 1.8% | | |
| PCH-6F | 7.2% | | |
| PCH-7F | 5.4% | | |
| CCP-20CF$_3$ | 7.2% | | |
| CCP-30CF$_3$ | 10.8% | | |
| CCP-40CF$_3$ | 6.3% | | |
| CCP-50CF$_3$ | 9.9% | | |
| PCH-5F | 9.0% | | |
| CWCQG-5-F | 10.0% | | |

| Example M17 | | | |
|---|---|---|---|
| BCH-3F.F | 10.8% | Clearing point [° C.]: | 97.8 |
| BCH-5F.F | 9.0% | Δn [589 nm, 20° C.]: | 0.0955 |
| ECCP-30CF$_3$ | 4.5% | Δε [1 kHz, 20° C.]: | 5.6 |
| ECCP-50CF$_3$ | 4.5% | | |
| CBC-33F | 1.8% | | |
| CBC-53F | 1.8% | | |
| CBC-55F | 1.8% | | |
| PCH-6F | 7.2% | | |
| PCH-7F | 5.4% | | |
| CCP-20CF$_3$ | 7.2% | | |
| CCP-30CF$_3$ | 10.8% | | |
| CCP-40CF$_3$ | 6.3% | | |
| CCP-50CF$_3$ | 9.9% | | |
| PCH-5F | 9.0% | | |
| CWCQG-3-OT | 10.0% | | |

| Example M18 | | | |
|---|---|---|---|
| BCH-3F.F | 10.8% | Clearing point [° C.]: | 98.2 |
| BCH-5F.F | 9.0% | Δn [589 nm, 20° C.]: | 0.0955 |
| ECCP-30CF$_3$ | 4.5% | Δε [1 kHz, 20° C.]: | 5.4 |
| ECCP-50CF$_3$ | 4.5% | | |
| CBC-33F | 1.8% | | |
| CBC-53F | 1.8% | | |
| CBC-55F | 1.8% | | |

-continued

| Example M18 | |
|---|---|
| PCH-6F | 7.2% |
| PCH-7F | 5.4% |
| CCP-20CF$_3$ | 7.2% |
| CCP-30CF$_3$ | 10.8% |
| CCP-40CF$_3$ | 6.3% |
| CCP-50CF$_3$ | 9.9% |
| PCH-5F | 9.0% |
| CWCQG-3-F | 10.0% |

What is claimed is:

1. A liquid-crystalline compound of formula I

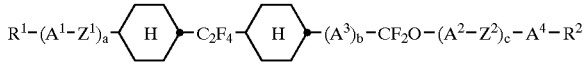

in which
R$^1$ and R$^2$ are each, independently of one another, an alkyl radical having from 1 to 15 carbon atoms which is unsubstituted, monosubstituted by CN or CF$_3$ or at least monosubstituted by halogen, where, in addition, one or more CH$_2$ groups are each optionally replaced by —O—, —S—, —CH=CH—, —C≡C—, —OC—O— or —O—CO— in such a way that O atoms are not linked directly to one another, and R$^2$ can also be CN, SF$_5$, F, Cl, NCS or SCN,
A$^1$, A$^2$, A$^3$ and A$^4$ are
a) a 1,4-cyclohexenylene or 1,4-cyclohexylene radical, in which in each case one or two non-adjacent CH$_2$ groups are each optionally replaced by —O— or —S—,
b) a 1,4-phenylene radical, in which one or two CH are each optionally replaced by N,
c) a radical from the group consisting of piperidine-1,4-diyl, 1,4-bicyclo[2.2.2]octylene, naphthalene-2,6-diyl, decahydronaphthalene-2,6-diyl and 1,2,3,4-tetrahydronaphthalene-2,6-diyl,
where the radicals a), b) and c) are in each case unsubstituted or monosubstituted or polysubstituted by halogen atoms,
Z$^1$ and Z$^2$ are each, independently of one another, —CO—O—, —O—CO—, —CF$_2$O—, —OCF$_2$—, —CH$_2$O—, —OCH$_2$—, —CH$_2$CH$_2$—, —(CH$_2$)$_4$—, —C$_2$F$_4$—, —CH$_2$CF$_2$—, —CF$_2$CH$_2$—, —CF=CF—, —CH=CH—, —C≡C— or a single bond,
a is 0, 1 or 2,
b is 0, 1 or 2, and
c is 0, 1 or 2, where a+b+c is ≦2.

2. A liquid-crystalline compound according to claim 1, wherein R$^1$ is a straight-chain alkyl radical having from 1 to 7 carbon atoms or an alkenyl radical having from 2 to 10 carbon atoms.

3. A liquid-crystalline compound according to claim 1, wherein R$^2$ is H, F, Cl, CN, CF$_3$, SF$_5$, CF$_2$H, OCF$_3$, OCF$_2$H, OCFHCF$_3$, OCFHCFH$_2$, OCFHCF$_2$H, OCF$_2$CH$_3$, OCF$_2$CFH$_2$, OCF$_2$CF$_2$H, OCF$_2$CF$_2$CF$_2$H, OCF$_2$CF$_2$CFH$_2$, OCFHCF$_2$CF$_3$, OCFHCF$_2$CF$_2$H, OCF$_2$CF$_2$CF$_3$, OCF$_2$CHFCF$_3$ or OCClFCF$_2$CF$_3$.

4. A liquid-crystalline compound according to claim 1, wherein c=1.

5. A liquid-crystalline compound of formulae I1 to I24:
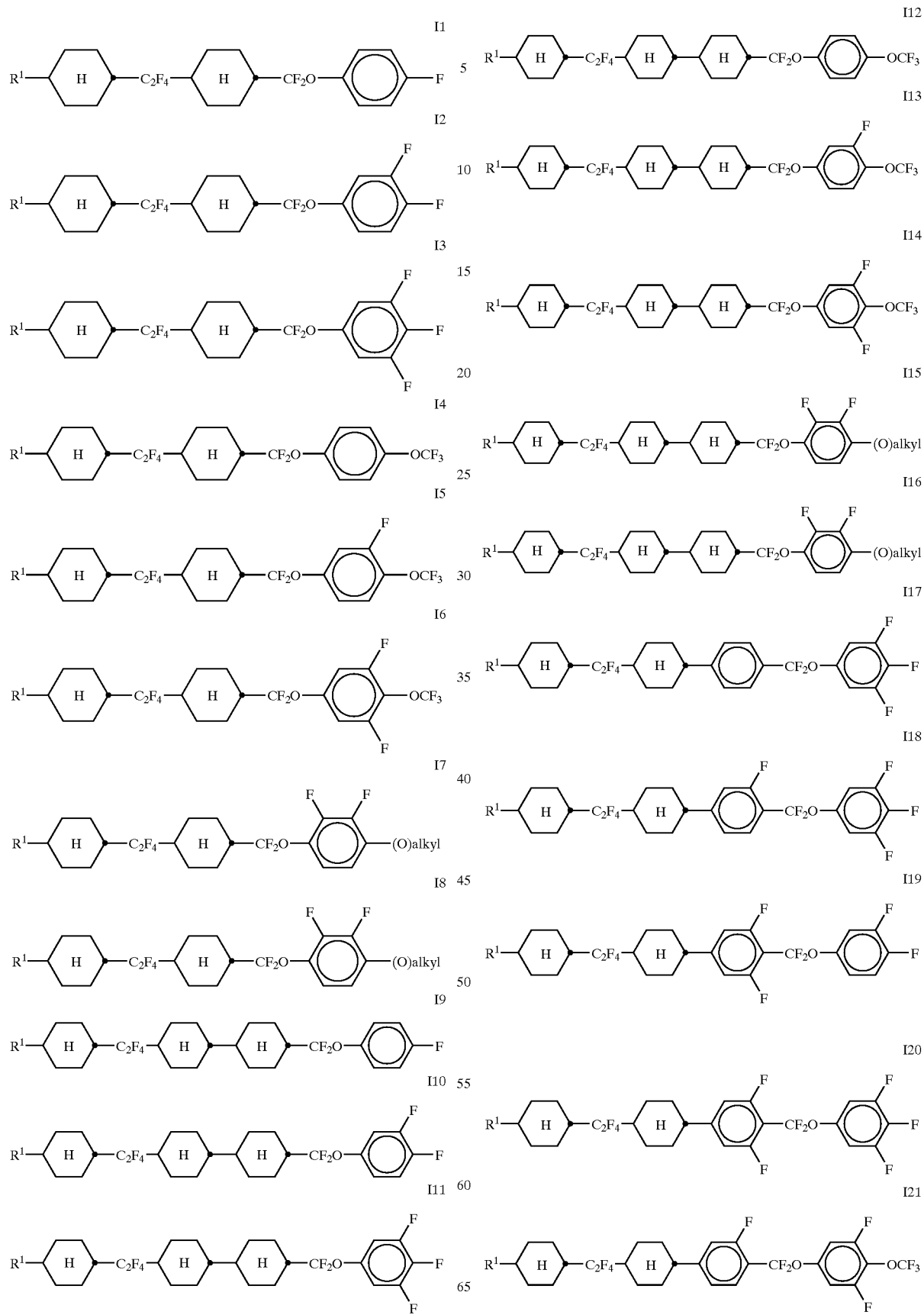

-continued

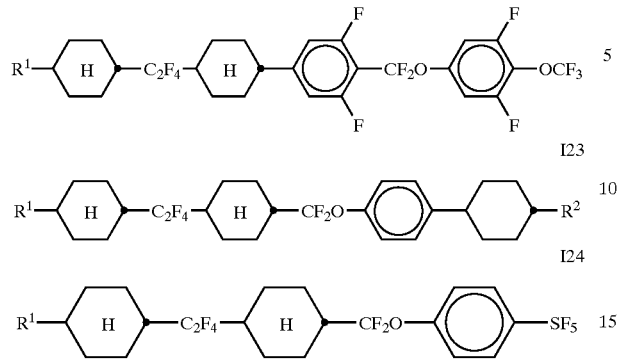

in which

R¹ is an alkyl radical having from 1 to 15 carbon atoms which is unsubstituted, monosubstituted by CN or CF₃ or at least monosubstituted by halogen, where, in addition, one or more CH₂ groups are each optionally replaced by —O—, —S—, —CH=CH—, —C≡C—, —OC—O— or —O—CO— in such a way that O atoms are not linked directly to one another, and "alkyl" is a straight-chain or branched alkyl radical having 1–9 carbon atoms.

6. A liquid-crystalline medium comprising at least two mesogenic compounds, wherein at least one of said compounds is a compound according to claim 1.

7. A liquid-crystalline medium according to claim 6, wherein said medium further comprises one or more compounds selected from formulae II, III, IV, V, VI, VII, VIII and IX:

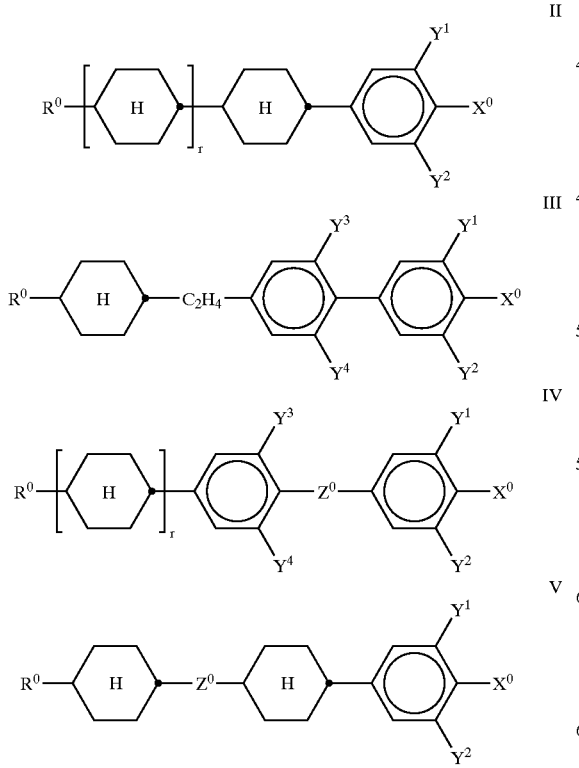

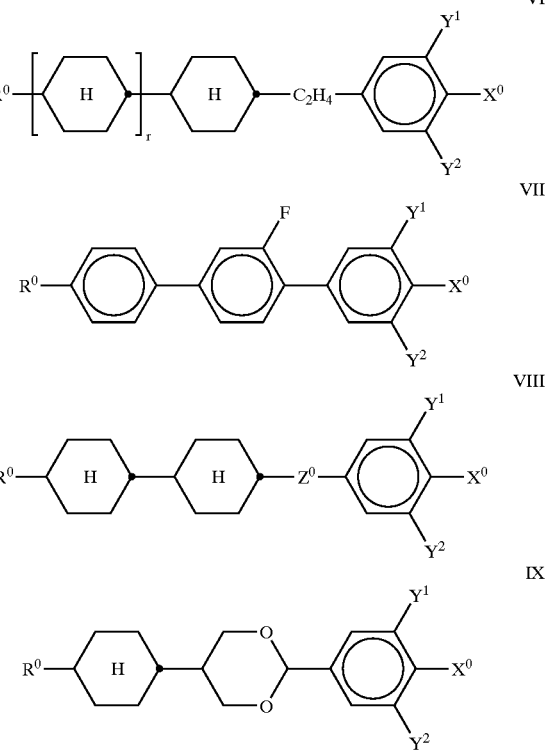

wherein

R⁰ is n-alkyl, oxaalkyl, fluoroalkyl, alkenyloxy or alkenyl, each having up to 9 carbon atoms, X⁰ is F, Cl or halogenated alkyl, halogenated alkenyl, halogenated alkenyloxy or halogenated alkoxy, each having up to 7 carbon atoms, Z₀ is —CH=CH—, —C₂H₄—, —C₂F₄—, —CF=CF—, —CF₂O—, —OCF₂— or —COO—,

Y¹, Y²,

Y³ and Y⁴ are each, independently of one another, H or F, and r is 0 or 1.

8. A medium according to claim 6, wherein the proportion of compounds of the formulae I to IX in the medium as a whole is at least 50% by weight.

9. A medium according to claim 6, wherein said medium further comprises one or more compounds of formulae RI to RX:

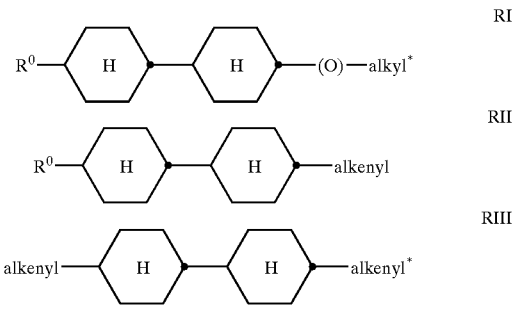

-continued

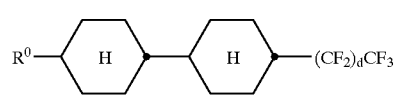
RIV

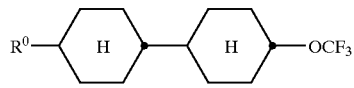
RV

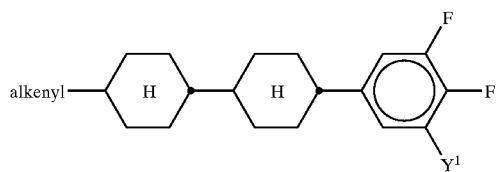
RVI

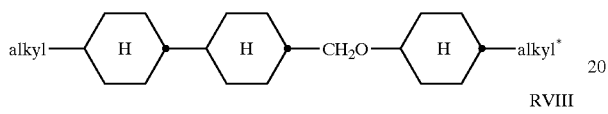
RVII

RVIII

RIX

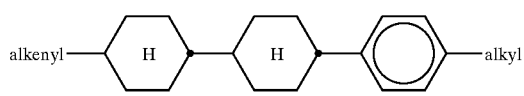
RX in which
$R^0$ is n-alkyl, oxaalkyl, fluoroalkyl, alkenyloxy or alkenyl, each having up to 9 carbon atoms,
d is 0, 1 or 2,
$Y^1$ is H or F,
alkyl or
alkyl* are each, independently of one another, a straight-chain or branched alkyl radical having 1–9 carbon atoms, and
alkenyl or
alkenyl* are each, independently of one another, a straight-chain or branched alkenyl radical having up to 9 carbon atoms.

10. A medium according to claim 7, wherein $X^0$ is F or $OCF_3$, and $Y^2$ is H or F.

11. In a method of generating an electro-optical effect using a liquid-crystalline medium, the improvement wherein said liquid-crystalline medium is according to claim 6.

12. An electro-optical liquid-crystal display containing a liquid-crystalline medium, wherein said medium is according to claim 6.

13. A liquid-crystalline compound according to claim 2, wherein $R^2$ is H, F, Cl, CN, $CF_3$, $SF_5$, $CF_2H$, $OCF_3$, $OCF_2H$, $OCFHCF_3$, $OCFHCFH_2$, $OCFHCF_2H$, $OCF_2CH_3$, $OCF_2CFH_2$, $OCF_2CF_2H$, $OCF_2CF_2CF_3$, $OCF_2CF_2CFH_2$, $OCFHCF_2CF_3$, $OCFHCF_2CF_2H$, $OCF_2CF_2CF_3$, $OCF_2CHFCF_3$ or $OCClFCF_2CF_3$.

14. A liquid-crystalline compound according to claim 2, wherein c is 1.

15. A liquid-crystalline compound according to claim 3, wherein c is 1.

16. A liquid-crystalline compound according to claim 13, wherein c is 1.

17. A medium according to claim 7, wherein the proportion of compounds of the formulae I to IX in the medium as a whole is at least 50% by weight.

18. A medium according to claim 7, wherein said medium further comprises one or more compounds of formulae RI to RX:

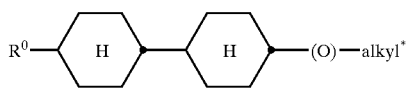
RI

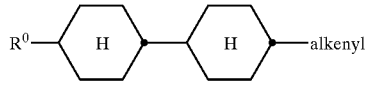
RII

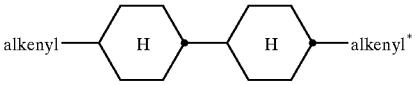
RIII

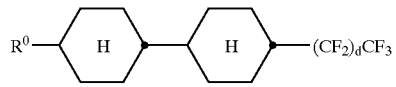
RIV

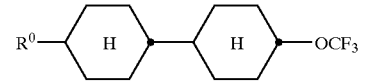
RV

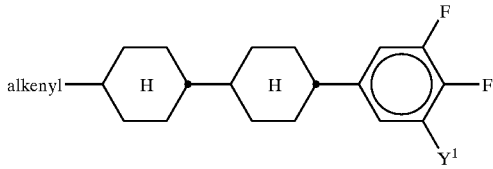
RVI

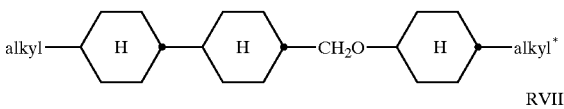
RVII

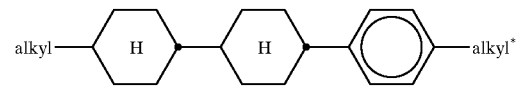
RVIII

RIX

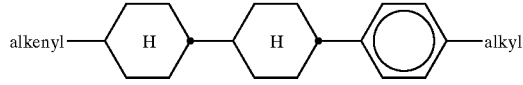
RX in which
$R^0$ is n-alkyl, oxaalkyl, fluoroalkyl, alkenyloxy or alkenyl, each having up to 9 carbon atoms,
d is 0, 1 or 2,
$Y^1$ is H or F,
alkyl or
alkyl* are each, independently of one another, a straight-chain or branched alkyl radical having 1–9 carbon atoms, and
alkenyl or
alkenyl* are each, independently of one another, a straight-chain or branched alkenyl radical having up to 9 carbon atoms.

19. A medium according to claim 8, wherein said medium further comprises one or more compounds of formulae RI to RX:

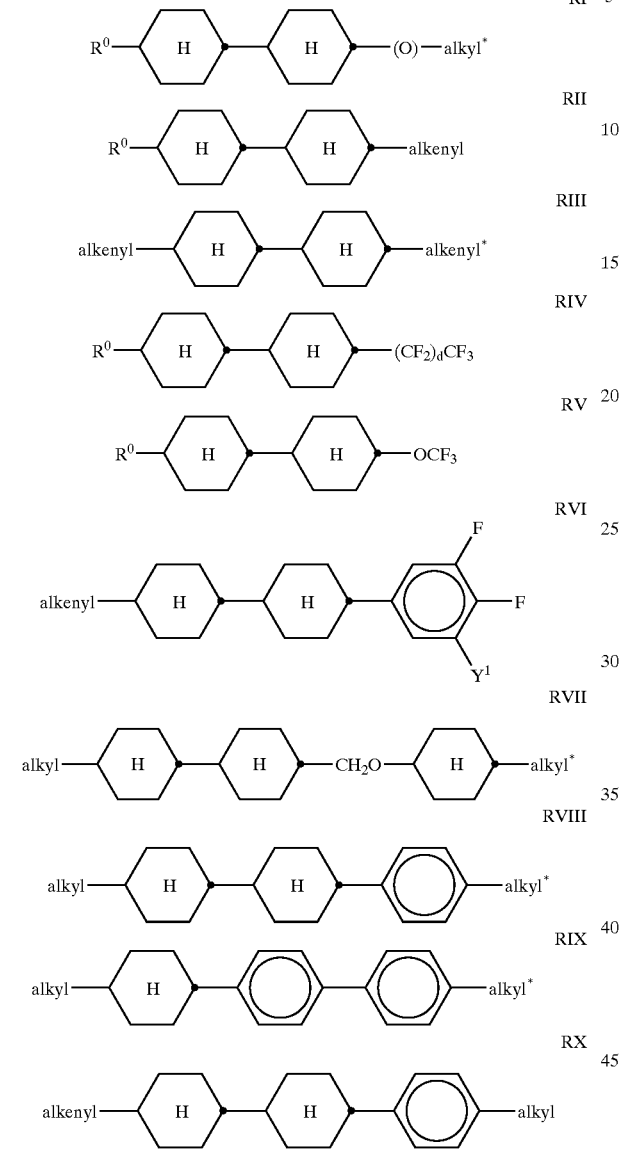

in which
R⁰ is n-alkyl, oxaalkyl, fluoroalkyl, alkenyloxy or alkenyl, each having up to 9 carbon atoms,
d is 0, 1 or 2,
$Y^1$ is H or F,
alkyl or
alkyl* are each, independently of one another, a straight-chain or branched alkyl radical having 1–9 carbon atoms, and
alkenyl or
alkenyl* are each, independently of one another, a straight-chain or branched alkenyl radical having up to 9 carbon atoms.

20. A medium according to claim 17, wherein said medium further comprises one or more compounds of formulae RI to RX:

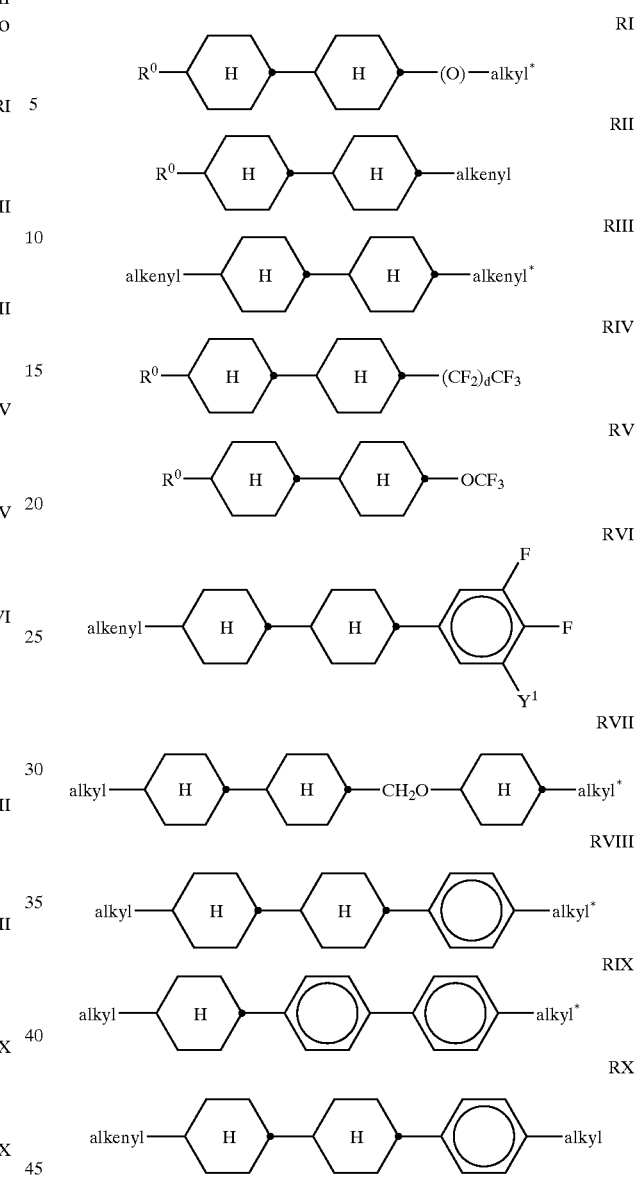

in which
R⁰ is n-alkyl, oxaalkyl, fluoroalkyl, alkenyloxy or alkenyl, each having up to 9 carbon atoms,
d is 0, 1 or 2,
$Y^1$ is H or F,
alkyl or
alkyl* are each, independently of one another, a straight-chain or branched alkyl radical having 1–9 carbon atoms, and
alkenyl or
alkenyl* are each, independently of one another, a straight-chain or branched alkenyl radical having up to 9 carbon atoms.

21. A compound according to claim 1, wherein $R^1$ is alkyl having from 1 to 10 carbon atoms or an alkenyl radical having from 2 to 10 carbon atoms.

22. A compound according to claim 1, wherein $Z^1$ and $Z^2$ are each a single bond, —CF₂O—, —OCF₂—, —C₂F₄—, —CH₂O—, —OCR₂— or —COO—.

23. A compound according to claim 1, wherein a is 0.

24. A compound according to claim 1, wherein $R^2$ is F, CN, $OCF_3$, $OCHF_2$, $CF_3$, $OCHFCF_3$, $OC_2F_5$, $OCF_2CHFCF_3$, or straight-chain alkyl or alkoxy.

25. A compound according to claim 1, wherein $R^1$ is straight-chain unsubstituted alkyl, alkoxy, alkenyloxy or alkenyl, in each case having up to 10 carbon atoms.

26. A compound according to claim 1, wherein $A^2$ is Phe, PheF, PheFF, Cyc, Che, Pyr, Dio, Dec or Nap, Cyc is 1,4-cyclohexylene, Che is 1,4-cyclohexenylene, Dio is 1,3-dioxane-2,5-diyl, Phe is 1,4-phenylene radical, Pyr is pyrimidine-2,5-diyl, PheF is 2- or 3-fluoro-1,4-phenylene, PheFF is 2,3-difluoro- or 2,6-difluoro-1,4-phenylene, Nap is substituted or unsubstituted naphthalene, and Dec is decahydronaphthalene.

27. A compound according to claim 1, wherein said compound contains not more than one of the radicals Bi, Pyd, Pyr, Dio, Dit, Nap or Dec, Dio is 1,3-dioxane-2,5-diyl, Dit is 1,3-dithiane-2,5-diyl, Pyd is pyridine-2,5-diyl, Pyr is pyrimidine-2,5-diyl, Bi is bicyclo[2.2.2]octylene, Nap is substituted or unsubstituted naphthalene, and Dec is decahydronaphthalene.

28. A compound according to claim 1, wherein $A^1$ is 2-fluoro-1,4-phenylene, 3-fluoro-1,4-phenylene, 2,3-difluoro-1,4-phenylene or 2,6-difluoro-1,4-phenylene.

29. A medium according to claim 6, wherein said medium has a nematic phase down to −20° C., a clearing point above 80° C., and a dielectric anisotropy value $\Delta\in$ of $\geq 4$.

30. A medium according to claim 29, wherein said medium has a nematic phase down to −30° C., and a clearing point above 90° C.

31. A medium according to claim 29, wherein said medium has a nematic phase down to −40° C., and a clearing point above 100° C.

32. A medium according to claim 29, wherein said medium has a dielectric anisotropy values $\Delta\in$ of $\geq 6$.

33. A medium according to claim 6, wherein said medium has a TN threshold below 1.5 V.

34. A medium according to claim 6, wherein said medium has a TN threshold below 1.3 V.

35. A medium according to claim 6, wherein the proportion of compounds of formula I in the medium as a whole is 5 to 50% by weight.

36. A medium according to claim 7, wherein the proportion of compounds of the formulae II to IX in the medium as a whole is 30 to 70% by weight.

* * * * *

UNITED STATES PATENT AND TRADEMARK OFFICE
CERTIFICATE OF CORRECTION

PATENT NO. : 6,780,477 B2
DATED : August 24, 2004
INVENTOR(S) : Peer Kirsch et al.

It is certified that error appears in the above-identified patent and that said Letters Patent is hereby corrected as shown below:

Column 76,
Line 41, delete "$Z_o$" and insert -- $Z^\circ$ --,

Column 80,
Line 66, delete "-$OCR_2$" and insert -- $OCR_2$ --,

Signed and Sealed this

First Day of February, 2005

JON W. DUDAS
*Director of the United States Patent and Trademark Office*